United States Patent [19]
Kennedy

[11] Patent Number: 5,990,097
[45] Date of Patent: Nov. 23, 1999

[54] METHODS OF TREATING ASTHMA WITH O-DESULFATED HEPARIN

[75] Inventor: Thomas P. Kennedy, Richmond, Va.

[73] Assignee: Cavalier Pharmaceuticals, Richmond, Va.

[21] Appl. No.: 08/887,989

[22] Filed: Jul. 3, 1997

Related U.S. Application Data

[60] Provisional application No. 60/024,391, Jul. 29, 1996.

[51] Int. Cl.$^6$ .................................................. A61K 31/725
[52] U.S. Cl. ................................................................ 514/56
[58] Field of Search .................................................. 514/56

[56] References Cited

U.S. PATENT DOCUMENTS

| | | | |
|---|---|---|---|
| 5,296,471 | 3/1994 | Holme et al. | 514/56 |
| 5,380,716 | 1/1995 | Conrad et al. | 514/56 |

FOREIGN PATENT DOCUMENTS

WO9319734A-1 10/1993 WIPO.

OTHER PUBLICATIONS

Diamant, Z., et al., Effect of Inhaled Heparin on Allergen–induced Early and Late Asthmatic Responses in Patients with Atopic Asthma, *Amer.Resp.Crit.Care Med.*, vol. 153, pp. 1790–1795 (1996).

Ahmed, T., et al., Effects of Inhaled Heparin on Immunologic and Nonimmunologic Bronchoconstrictor Responses in Sheep, *Am.Rev.Respir.Dis.*, vol. 145, pp. 566–570 (1992).

Jacoby, D.B., et al., Human Eosinophil Major Basic Protein is an Endogenous Allosteric Antagonist at the Inhibitory Muscarinic M2 Receptor, *J.Clin.Invest.*, vol. 91, pp. 1314–1318 (1993).

Bowler, S.D., et al., Heparin Inhibits the Immediate Response to Antigen in the Skin and Lungs of Allergic Subjects, *Am.Rev.Respir.Dis.*, vol. 147, pp. 160–163 (1993).

Ahmed, T., et al., Preventing Bronchoconstriction in Exercise–Induced Asthma with Inhaled Heparin, *N.Engl.J.Med.*, vol. 329(2), pp. 90–95 (1993).

Minette, P.A.H., et al., A Muscarinic Agonist Inhibits Reflex Brochoconstriction in Normal But Not in Asthmatic Subjects, *J.Appl.Physiol.*, vol. 67(6), pp. 2461–2465 (1989).

Ahmed, T., et al., Inhibition of Antigen–Induced Airway and Cutaneous Responses by Heparin: A Pharmacodynamic Study, *J.Appl.Physiol.*, vol. 74(4), pp. 1492–1498 (1993).

Jaseja, M., et al., Novel Regio– and Stereoselective Modifications of Heparin in Alkaline Solution. Nuclear Magnetic Resonance Spectroscopic Evidence, *Can.J.Chem.*, vol. 67, pp. 1449–1456 (1989).

Hu, J., et al., Complex Allosteric Modulation of Cardiac Muscarinic Receptors by Protamine: Potential Model for Putative Endogenous Ligands, *Mol.Pharmacol.*, vol. 42, pp. 311–324 (1992).

Jacques, L.B., et al., Intrapulmonary Heparin—A New Procedure for Anticoagulant Therapy, *Lancet,* Nov. 27, 1976, pp. 1157–1161.

Dolowitz, D.A., et al., The Use of Heparin in the Control of Allergies, *Annals. of Allergy,* vol. 23, pp. 309–313 (1965).

Fryer, A.D., et al., Function of Pulmonary $M_2$ Muscarinic Receptors in Antigen–Challenged Guinea Pigs is Restored by Heparin and Poly–L–Glutamate, *J.Clin.Invest.,* vol. 90, pp. 2292–2298 (1992).

Hartman, M.M., Thrombo–Embolic Phenomena In Severe Asthma, *California Medicine,* vol. 98(1), pp. 27–32 (1963).

Rej, R., et al., Importance for Blood Anticoagulant Activity Of A 2–Sulfate Group On L–Iduronic Acid Residues In Heparin, *Thrombosis and Haemostasis,* vol. 61, p. 540 (1989).

(List continued on next page.)

*Primary Examiner*—Raymond Henley, III
*Attorney, Agent, or Firm*—Alston & Bird LLP

[57] ABSTRACT

A method for reducing asthmatic response in a mammal comprising administering a response-reducing amount of O-desulfated heparin to the mammal, thereby reducing the asthmatic response. The amount can be administered by aerosolization. The O-desulfated heparin has O-desulfation at least at the 2-O and 3-O positions.

34 Claims, 11 Drawing Sheets

OTHER PUBLICATIONS

Edens, R.E., et al., Heparin Is Not Just an Anticoagulant Anymore: Six and One–Half Decades of Studies on the Ability of Heparin to Regulate Complement Activity, *Complement Today: Complement Profiles,* vol. 1, pp. 96–120 (1993).

Rej, R., et al., Base–Catalyzed Conversion of the α–L–Iduronic Acid 2–Sulfate Unit of Heparin Into a Unit of α–L–galacturonic Acid, and Related Reactions, *Carbohydr Res,* vol. 200, pp. 437–447 (1990).

Rao, N., et al., Sulfated Polysaccharides Prevent Human Leukocyte Elastase—Induced Acute Lung Injury and Emphysema on Hamsters, *Am.Rev. Respir. Dis.,* vol. 142, pp. 407–412 (1990).

Redini, F., et al., Inhibition of Leucocyte Elastase By Heparin and Its Derivatives, *Biochem. J.,* vol. 252, pp. 515–519 (1988.

5,990,097

METHODS OF TREATING ASTHMA WITH O-DESULFATED HEPARIN

The present application claims priority to provisional application U.S. Ser. No. 60/024,391, filed Jul. 29, 1996.

FIELD OF THE INVENTION

The present invention relates to the field of treating and preventing asthmatic response.

BACKGROUND ART

Asthma is an inflammatory disease of lung airways that makes the airways prone to narrow too much and too easily in response to a wide variety of provoking stimuli. In the lung, the major innervating sensory and motor nervous system is contained within the vagus nerve (FIG. 1). Exposure of the airway to irritants such as sulfur dioxide, prostaglandins, histamine and cold air can stimulate afferent sensory fibers of the vagus nerve, thereby setting off bronchoconstriction, or airway narrowing, due to reflex release of acetylcholine by cholinergic efferent motor branches of the vagus nerve. While this reflex is present in normal individuals, it is greatly exaggerated in asthmatic patients. This exaggerated narrowing is often called airways hyperreactivity.

Airways hyperreactivity in asthmatic patients and in animal models of asthma is thought to arise from increased release of the endogenous neurotransmitter acetylcholine from the efferent motor vagus nerve endings innervating the airway (A. D. Fryer, et al., *Journal of Clinical Investigation* (1992) 90:2292–2298). In the airway, release of acetylcholine from the vagus nerves is under the local control of inhibitory muscarinic autoreceptors on the postganglionic nerves (FIG. 1). These autoreceptors are called $M_2$ muscarinic receptors, while the muscarinic receptors on airway smooth muscle are $M_3$ receptors. Thus, acetylcholine released from the vagus nerve stimulates both $M_3$ muscarinic receptors on airway smooth muscle, causing bronchoconstriction, and $M_2$ muscarinic receptors on the nerves, decreasing further release of acetylcholine. In asthmatics, inhibitory $M_2$ muscarinic receptors are dysfunctional, resulting in exaggerated acetylcholine release and, therefore, exaggerated bronchoconstriction, or airways hyperreactivity, in response to a given irritant airway stimulus (A. D. Fryer, el al., *Journal of Clinical Investigation* (1992) 90:2292–2298; D. B. Jacoby, el al., *Journal of Clinical Investigation* (1993) 91:1314–1318).

The negative feedback control of acetylcholine release provided by the $M_2$ muscarinic receptor can be demonstrated experimentally by measuring vagally induced bronchoconstriction in the presence of selective muscarinic agonists or antagonists. Blockade of neuronal muscarinic $M_2$ receptors with gallamine potentiates vagally induced bronchoconstriction. Conversely, the selective muscarinic $M_2$ receptor antagonist pilocarpine inhibits irritant-induced cholinergic reflex bronchoconstriction in normal subjects. This inhibitory mechanism is not present in asthmatics because of dysfunctional $M_2$ receptors (P. A. Minette, et al., *Journal of Applied Physiology* (1989) 67:2461–2465). Such a defect in muscarinic autoreceptors results in exaggerated cholinergic reflexes in asthma, because the normal feedback inhibition of acetylcholine release is lost.

$M_2$ receptor dysfunction and subsequent airways hyperreactivity in asthma is thought to be due to increased susceptibility of the receptor to damage by products of the inflammatory response in the airway. Asthma results in an influx of inflammatory cells, especially eosinophils, into the airway. Activated eosinophils in asthmatics secrete a number of injurious proteins, including major basic protein, eosinophil peroxidase, and eosinophil cationic protein. All of these proteins are strongly positively charged. These and other positively charged proteins can cause airway hyperresponsiveness (R. H. Gundel, et al., *Journal of Clinical Investigation* (1991) 87:1470–1473; A. J. Coyle, et al., *American Review of Respiratory Diseases* (1993) 147:896–900). Major basic protein (D. B. Jacoby, et al., *Journal of Clinical Investigation* (1993) 91:1314–1318) and other positively charged proteins (J. Hu, el al. *Molecular Pharmacology* (1992) 42:311–324) have been shown to function as $M_2$ muscarinic receptor antagonists. Thus, airways hyperreactivity in asthma is a consequence of direct antagonism of inhibitory $M_2$ cholinergic receptors by components of airway inflammation.

The treatment of airways hyperreactivity in asthma is currently directed against either inhibiting the airway inflammation leading to release of products that inhibit $M_2$ receptors, or toward direct reversal of bronchoconstriction of airway smooth muscle. Corticosteroids are the mainstay of anti-inflammatory therapy. Beta-adrenergic agonists, acting by stimulation of $beta_2$ adrenergic receptors on airway smooth muscle, are used as bronchodilators to directly reverse constricted airways. Nonselective anti-cholinergic drugs such as atropine and ipratropium bromide are available for use as bronchodilators, but block both prejunctional $M_2$ receptors and $M_3$ receptors on smooth muscle with equal efficacy. This increases acetylcholine release, overcoming the postjunctional blockade, and makes these nonselective anti-cholinergic agents ineffective at reversing vagally mediated bronchoconstriction. A more specific treatment for reversing the $M_2$ receptor blockade would be of great benefit as a treatment for the airways hyperreactivity of asthma.

Recently, the anticoagulant drug heparin has been shown to reverse antigen-induced $M_2$ receptor dysfunction in antigen-challenged guinea pigs (A. D. Fryer, et al., *Journal of Clinical Investigation* (1992) 90:2292–2298) and to reverse binding of $M_2$ receptor by major basic protein it vitro (D. B. Jacoby, el al., *Journal of Clinical Investigation* (1993) 91:1314–1318). Heparin has over the years been suggested as a treatment for asthma (M. M. Hartman, *California Medicine* (1 963) 98:27–32; D. A. Dolowitz, et al., *Annals of Allergy* (1 965) 23:309–313; T. Ahmed, el al., *American Review of Respiratory Diseases* (1992) 145:566–570; T. Ahmed, el al., *Journal of Applied Physiology* (1993) 74:1492–1498; S. D. Bowler, et al., *American Review of Respiratory Diseases* (1993) 147:160–163; T. Ahmed, el al., *New England Journal of Medicine*; International PCT Application, PCT/US93/02880). However, as a treatment for the airways hyperreactivity of asthma, heparin has one great disadvantage: it is an anticoagulant. As such, it would expose the treated patient to an unacceptable risk of hemorrhage, even if treatment was localized by aerosolization of heparin into the lung airway. Aerosolized heparin is well absorbed into the systemic circulation, and administration of heparin by lung aerosolization has been advocated as a method of anticoagulating the blood (L. B. Jaques, el al., *Lancet* (1976) ii:157–1161).

To use heparin safely as a treatment for the airways hyperreactivity of asthma, it would need to be first inactivated as an anticoagulant without affecting its efficacy to treat asthma. Several chemical methods exist for inactivating heparin as an anticoagulant. Most are based on techniques of chemical desulfation, since it is well established that sulfate groups of heparin are important for anticoagulant activity. However, N-desulfated heparin has been previously reported to be ineffective in the prevention of asthmatic-like bronchoconstriction from aerosolized antigen (T. Ahmed, et al., *American Review of Respiratory Diseases* (1992) 145:566–570, see FIG. 2). Additionally, N-desulfated heparin has been previously reported to be only 50% as effective as heparin in complement inhibition (J. M. Weiler et al., *J.Immunol.* (1992) 148:3210–3215; R. E. Edens et al. *Complement Today* (Cruse, J. M. and Lewis, R. E. Jr. eds): *Complement Profiles* (1993) 1:96–120).

Thus, the literature teaches that chemical desulfation would not be an effective strategy in modifying heparin for use as an effective treatment for asthmatic airways hyperreactivity. In contrast to what would be predicted by the literature, the present invention discloses that, surprisingly, selective O-desulfation of heparin eliminates the anticoagulant activity of heparin without destroying the ability of heparin to reverse $M_2$ muscarinic receptor blockade in asthma.

Asthma has been long described in the medical literature as an episodic disease characterized by reversible airways obstruction. This is in contrast to chronic obstructive airways disease from chronic bronchitis and emphysema, in which physiologic airways obstruction is permanent and slowly progressive. However, the characterization of airways obstruction in asthma as episodic and reversible may be simplistic. Clinical pulmonary physicians have recently begun to appreciate a population of asthmatics, usually older individuals, who appear to have unrelenting disease, with lung function that never normalizes between acute bronchospastic episodes. Some of these patients appear to progress to fixed airways obstruction without the presence of other known risk factors such as active or past cigarette smoking. This population presents a difficult clinical challenge, in that many of these individuals are steroid dependent or even relatively resistant to intervention with steroids and other anti-inflammatory or bronchodilator medications.

One possible explanation for this difficult-to-treat population is that patients with chronic asthma undergo remodeling of their airways, with substantial increase in the amount of smooth muscle in airway walls (Heard, B. E., and S. Hossain. 1973. Hyperplasia of bronchial muscle in asthma. *J. Path.* 110:319–331, James, A. L., P. D. Pare, and J. C. Hogg. 1989. The mechanics of airway narrowing in asthma. *Am. Rev. Respir. Dis.* 139:242–246; Saetta, M., A. DiStefano, C. Rosina, G. Thiene, and L. M. Fabbri. 1991. Quantitative structural analysis of peripheral airways and arteries in sudden fatal asthma. *Am. Rev. Respir. Dis.* 143:138–143; Ollerenshaw, S. L., and A. J. Woolcock. 1992. Characteristics of the inflammation in biopsies from large airways of subjects with asthma and subjects with chronic airflow limitation. *Am. Rev. Respir. Dis.* 145:922–927). Patients dying of asthma have over twice the amount of airway smooth muscle as nonasthmatic subjects (Saetta, M., A. DiStefano, C. Rosina, G. Thiene, and L. M. Fabbri. 1991. Quantitative structural analysis of peripheral airways and arteries in sudden fatal asthma. *Am. Rev. Respir. Dis.* 143:138–143), and airway smooth muscle hypertrophy is seen in sensitized Brown-Norway rats (Sapienza, S., T. Du, D. H. Eidelman, N. S. Wang, and J. G. Martin. 1991. Structural changes in the airways of sensitized Brown Norway rats after antigen challenge. *Am. Rev. Respir. Dis.* 144:423–427; Wang, C. G., T. Du, L. J. Xu, and J. G. Martin. 1993. Role of leukotriene $D_4$ in allergen-induced increases in airway smooth muscle in the rat. *Am. Rev. Respir. Dis.* 148:413–417) and cats (Padrid, P., S. Snook, T. Finucane, P. Shiue, P. Cozzi, J. Solway, and A. R. Leff. 1995. Persistent airway hyperresponsiveness and histologic alterations after chronic antigen challenge in cats. *Am. J. Respir. Crit. Care Med.* 151:184–193) after antigen challenge. Increased airway smooth muscle might be expected to change the counterbalance of forces tending to distend or close the airway lumen, thereby altering the location of the equal pressure point, when air is unable to flow (Pride, N. B., S. Permutt, R. L. Riley, and B. Bromberger-Barnea. 1967. Determinants of maximal expiratory flow from the lungs. *J. Appl. Phlysiol* 23:646–662). Airway wall thickening has also been proposed as a partial explanation for exaggerated changes in airway caliber when airway smooth muscle shortens (James, A. L., P. D. Pare, and J. C. Hogg. 1989. The mechanics of airway narrowing in asthma. *Am. Rev. Respir. Dis.* 139:242–246). Even small changes in airway wall thickness that have little effect on baseline resistance to airflow can produce an increase in maximal airway responsiveness to agonists, similar to that seen in asthmatics (Moreno, R. H., J. C. Hogg, and P. D. Pare. 1985. Mechanisms of airway narrowing. *Am. Rev. Respir. Dis.* 133:1171–1180).

The precise stimuli for airway smooth muscle hypertrophy in asthma are unclear, but several possible mitogens for airway smooth muscle have been demonstrated, including endothelin, histamine, the mast cell enzyme tryptase and leukotrienes (Wang, C. G., T. Du, L. J. Xu, and J. G. Martin. 1993. Role of leukotriene $D_4$ in allergen-induced increases in airway smooth muscle in the rat. *Am. Rev. Respir. Dis.* 148:413–417; Vitori, E. N., M. Marini, A. Fasoli, R. De Franchia, and S. Mattoli. 1992. Increased expression of endothelin in bronchial epithelial cells of asthmatic patients and effect of corticosteroids. *Am. Rev. Respir. Dis.* 146:1320–1325; Noveral, J. P., S. M. Rosenberg, R. A. Anbar, N. A. Pawlowski, and M. M. Grunstein. 1992. Role of endothelin-1 in regulating proliferation of cultured rabbit airway smooth muscle cells. *Am. J. Physiol.* 263(*Lung Cell. Mol Physiol.* 7):L317–L324; Glassberg, M. K., A. Ergul, A. Wanner, and D. Puett. 1994. Endothelin-1 promotes mitogenesis in airway smooth muscle cells. *Am. J. Respir. Cell Mol. Biol.* 10:316–321; Panettieri, R. A., P. A. Yadvish, A. M. Kelly, N. A. Rubinstein, and M. I. Kotlikoff. 1990. Histamine stimulates proliferation of airway smooth muscle and induces c-fos expression. *Am. J. Physiol* 259 (Lung. Cell Mol. Physiol. 3):L365-L371; Ruoss, S. J., T. Hartmann, and G. Caughey. 1992. Mast cell tryptase is a mitogen for cultured fibroblasts. *J Clin. Invest.* 88:493–499) The polycation protamine is mitogenic for cultured vascular smooth muscle (Edelman, E. R., L. A. Pukac, and M. J. Karnovsky. 1993. Protamine and protamine-insulins exacerbate the vascular response to injury. *J Clin. Invest.* 91:2308–2313). Therefore, it is also possible that eosinophil-derived positively-charged polycations such as major basic protein might stimulate proliferation of airway smooth muscle.

Equally unclear is how airway smooth muscle remodeling in asthma might be prevented. The bronchodilator salbutamol inhibits proliferation of cultured human airway smooth muscle in response to thrombin and epidermal growth factor (Tomlinson, P. R., J. W. Wilson, and A. G. Stewart. 1994. Inhibition by salbutamol of the proliferation of human airway smooth muscle cells grown in culture. *Br. J. Pharmacol.* 111:641–647). However, in general, by preventing mast cell degranulation, beta adrenergic agonist bronchodilators may deprive the airway of the anti-proliferative effects of mast cell heparin release, thereby exacerbating smooth muscle remodeling (Page, C.P. 1991. One explanation of the asthma paradox: inhibition of natural anti-inflammatory mechanism by $B_2$-agonists. *Lancet* 337:717–720). In the chronically antigen challenged ovalbumin-sensitized Brown Norway rat, the leukotriene $D_4$ antagonist MK-571 reduces smooth muscle proliferation of small airways, but was only partially effective in preventing airway remodeling of larger airways (Wang, C. G., T. Du, L. J. Xu, and J. G. Martin. 1993. Role of leukotriene $D_4$ in allergen-induced increases in airway smooth muscle in the rat. *Am. Rev. Respir. Dis.* 148:413–417). Because more than one mitogen is likely to promote smooth muscle proliferation in asthmatic patients, it is not surprising that specific blockade of one mediator fails to prevent the remodeling process. For therapy, a treatment is needed that intervenes at a more focal control point in growth regulatory events.

Mast cell heparin has been proposed to normally modulate growth and proliferation of airway smooth muscle (Page, C.P. 1991. One explanation of the asthma paradox: inhibition of natural anti-inflammatory mechanism by $B_2$-agonists. *Lancet* 337:717–720). The closely related sulfated polysaccharide heparan sulfate has been shown to inhibit proliferation of cultured canine tracheal smooth muscle (Panettieri, R. A., P. A. Yadvish, A. M. Kelly, N. A. Rubinstein, and M. I. Kotlikoff. 1990. Histamine stimulates proliferation of airway smooth muscle and induces c-fos expression. *Am. J. Physiol.* 259 (*Lung Cell. Mol. Physiol.* 3):L365-L371). Heparin is a potent inhibitor of proliferation of vascular smooth muscle in vitro (Hoover, R. L., R. Rosenberg, W. Haering, and M. J. Karnovsky. 1980. Inhibition of rat arterial smooth muscle cell proliferation by heparin. *Cir. Res.* 47:578–583) and in vivo (Guyton, J. R., R. D. Rosenberg, A. W. Clowes, and Karnovsky. 1980. Inhibition of rat arterial smooth muscle cell proliferation by heparin. In vivo studies with anticoagulant and nonanticoagulant heparin. *Cir. Res.* 46:625–634; Clowes, A. W., and M. M. Clowes. 1985. Kinetics of cellular proliferation after arterial injury. II. Inhibition of smooth muscle growth by heparin. *Lab. Invest.* 42:611–616; Clowes, A. W., and M. M. Clowes. 1986. Kinetics of cellular proliferation after arterial injury. IV. Heparin inhibits rat smooth muscle mitogenesis and migration. *Circ. Res.* 58:839–845).

Recently, heparin and low molecular weight heparin have been demonstrated by Kilfeather el al. to be potent inhibitors of serum-induced proliferation of bovine tracheal smooth muscle cells in culture (Kilfeather, S. A., S. Tagoe, A. C. Perez, K. Okona-Mensa, R. Matin, and C. P. Page. 1995. Inhibition of serum-induced proliferation of bovine tracheal smooth muscle cells in culture by heparin and related glycosaminoglycans. *Brit. J. Pharamcol.* 114:1442–1446). In discussing structure-activity implications of their findings, Kilfeather and coworkers suggested that O-sulfation is required for antiproliferative activity in airway smooth muscle cells. Earlier, Wright et al, had shown that increasing the charge of inactive tetrasaccharide fragments by O-oversulfation made them antiproliferative against vascular smooth muscle, whereas reducing the charge of active larger fragments caused them to lose their antiproliferative activity (Wright, T. C., Jr., J. J. Castello, Jr., M. Petitou, J.-C. Lormeau, J. Choay, and M. J. Karnovsky. 1989. Structural determinants of heparin's growth inhibitory activity. Interdependence of oligosaccharide size and charge. *J Biol. Chem.* 264:1534–1542). Castellot et al, had suggested an absolute requirement for 3-O sulfation as a necessary structural requirement for heparin to inhibit vascular smooth muscle proliferation (Castellot, J. J., Jr., J. Choay, J.-C. Lormeau, M. Petitou, E. Sache, and M. J. Karnovsky. 1986. Structural determinants of the capacity of heparin to inhibit the proliferation of vascular smooth muscle cells. II. Evidence for a pentasaccharide sequence that contains a 3-O-sulfate group. *J. Cell Biol.* 102:1979–1984). Maccarana et al. reported the importance of 2-O sulfates for heparin binding of the mitogen basic fibroblast growth factor (Maccarana, M., B. Casu, and U. Lindahl. 1993. Minimal sequence in heparin/heparan sulfate required for binding of basic fibroblast growth factor. *J. Biol. Chem.* 268:23898–23905).

In contrast, the present invention provides the surprising discovery that a selectively 2-O, 3-O-desulfated heparin produced by alkaline lyophilization is a potent inhibitor of fetal calf serum stimulated-airway smooth muscle proliferation.

2-O-desulfated heparin has been reported to be made (R. Rej el al., *Thrombosis and Hemostasis* (1989)61:540; and M. Jaseja et al., *Canadian Journal of Chemistry* (1989) 67:1449–1456). Actually, those authors did not recognize that the compound they made was, in fact, 2-O as well as 3-O desulfated heparin. Briefly, the Rej et al. and Jaseja et al. method comprises starting with a heparin solution pH adjusted with 0.1 N sodium hydroxide, which is then lyophilized to produce a 2-O-desulfated alpha-L-iduronic acid residue (and a 3-O-desulfated glucosamine residue). The anticoagulant activity of heparin was studied; however, there was no suggestion of inhibition of airways reactivity or treatment of asthmatic conditions. Likewise, Rej el al. and Jaseja et al. disclosed no activity for 2-O, 3-O-desulfated heparin, and further, did not disclose any effective doses for the compound for any purpose.

SUMMARY OF THE INVENTION

It is an object of the present invention to provide a method for reducing or inhibiting airways hyperreactivity of asthmatic response in mammals comprising administering to the mammal a treatment effective amount of O-desulfated heparin having O-desulfation at least at the 2-O and 3-O positions, thereby reducing or inhibiting the airways hyperreactivity. It is an object of the invention to provide a method for increasing $M_2$ muscarinic receptor activity in an asthmatic mammal comprising administering a treatment effective amount of O-desulfated heparin. It is a further object of the present invention to provide a method for reducing or preventing bronchoconstriction in a mammal comprising administering a treatment effective amount of O-desulfated heparin. It is another object of the present invention to provide a method for inhibiting complement-mediated hemolysis in a mammal comprising administering a treatment effective amount of O-desulfated heparin. It is a further object of the present invention to provide a method for reducing or inhibiting airway smooth muscle proliferation in a mammal comprising administering to the mammal an airway smooth muscle cell proliferation-reducing or -inhibiting amount of O-desulfated heparin having O-desulfation at least at the 2-O and 3-O positions, thereby reducing or inhibiting the airway smooth muscle cell proliferation in the mammal. It is another object of the present invention to provide such methods which substantially do not induce anti-coagulant activity.

Consideration of the specification, including the several figures and examples to follow will enable one skilled in the art to determine additional objects and advantages of the invention.

ACh, acetylcholine; N, nicotinic receptor; $M_1$, $M_1$ muscarinic receptor; $M_2$, $M_2$ muscarinic receptor; $M_3$, $M_3$ muscarinic receptor; arrows indicate neurotransmission.

Figure 2:
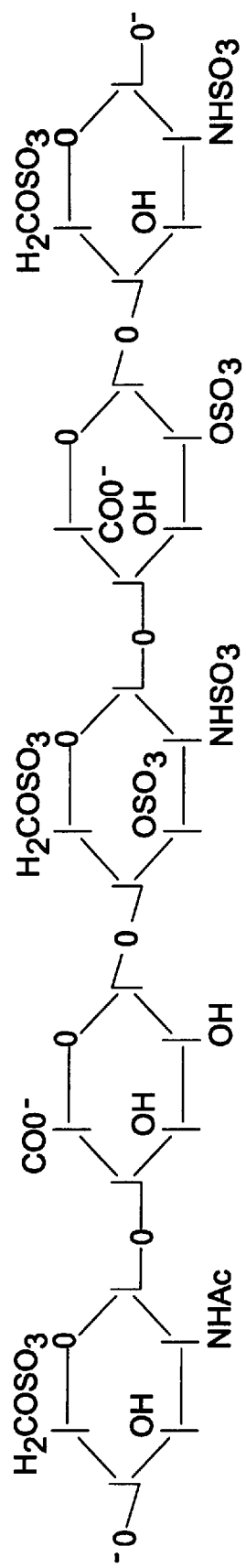

FIG. 2 shows a chemical formula of the pentasaccharide binding sequence of naturally occurring heparin.

Figure 3:
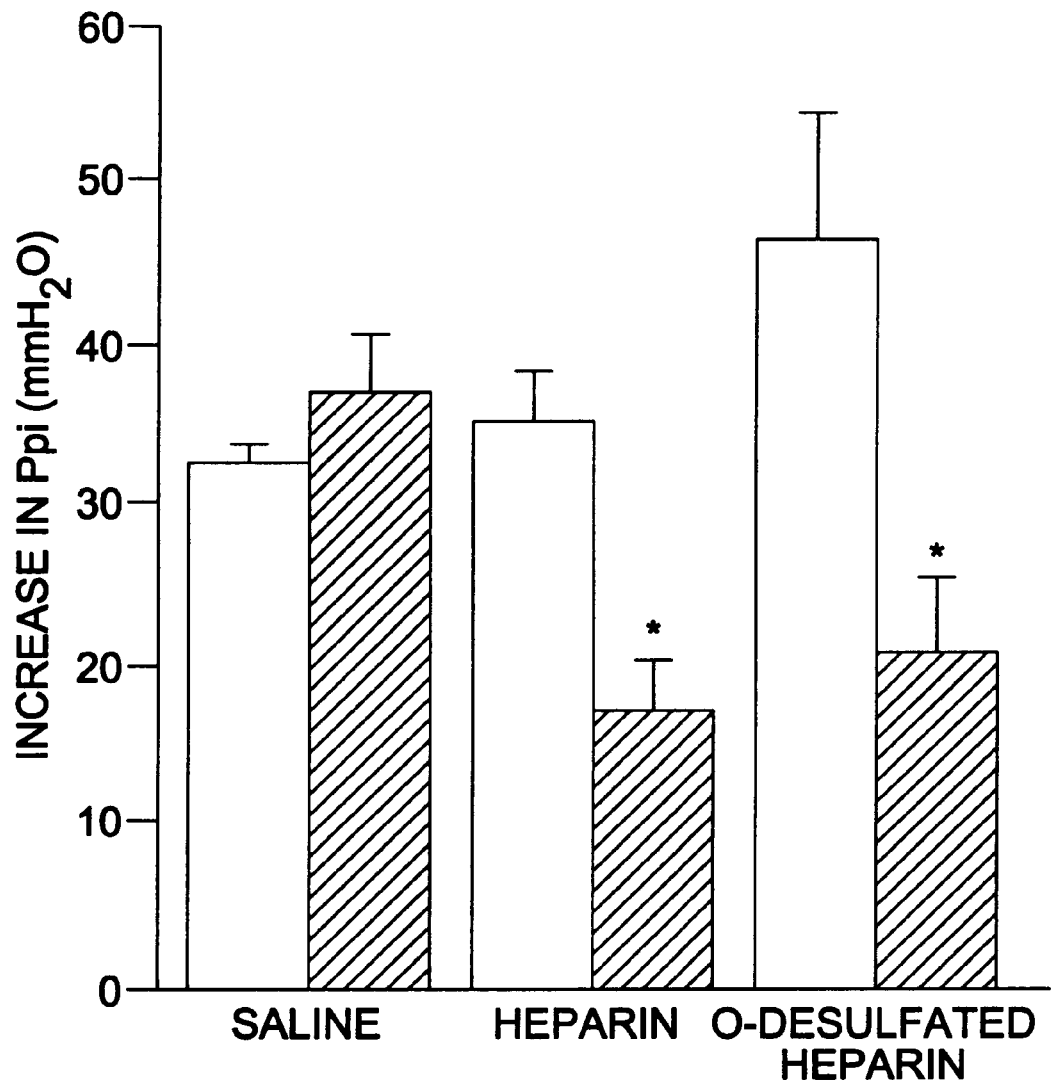

FIG. 3 shows a graph of the inhibition of vagally-induced bronchoconstriction by heparin and O-desulfated heparin in sensitized asthmatic guinea-pigs challenged with ovalbumin. Open columns show vagal bronchoconstriction in the absence of treatment. Filled columns show the effect of treatment with saline, fully anticoagulant heparin (2,000 U/kg) or O-desulfated heparin (91.2 mg/kg) on vagally induced bronchoconstriction. Data are mean with s.e. mean shown by vertical bars, n=5 for saline, 4 for heparin, and 5 for O-desulfated heparin. *P<0.05, using, paired Student's t-test.

Figure 4:
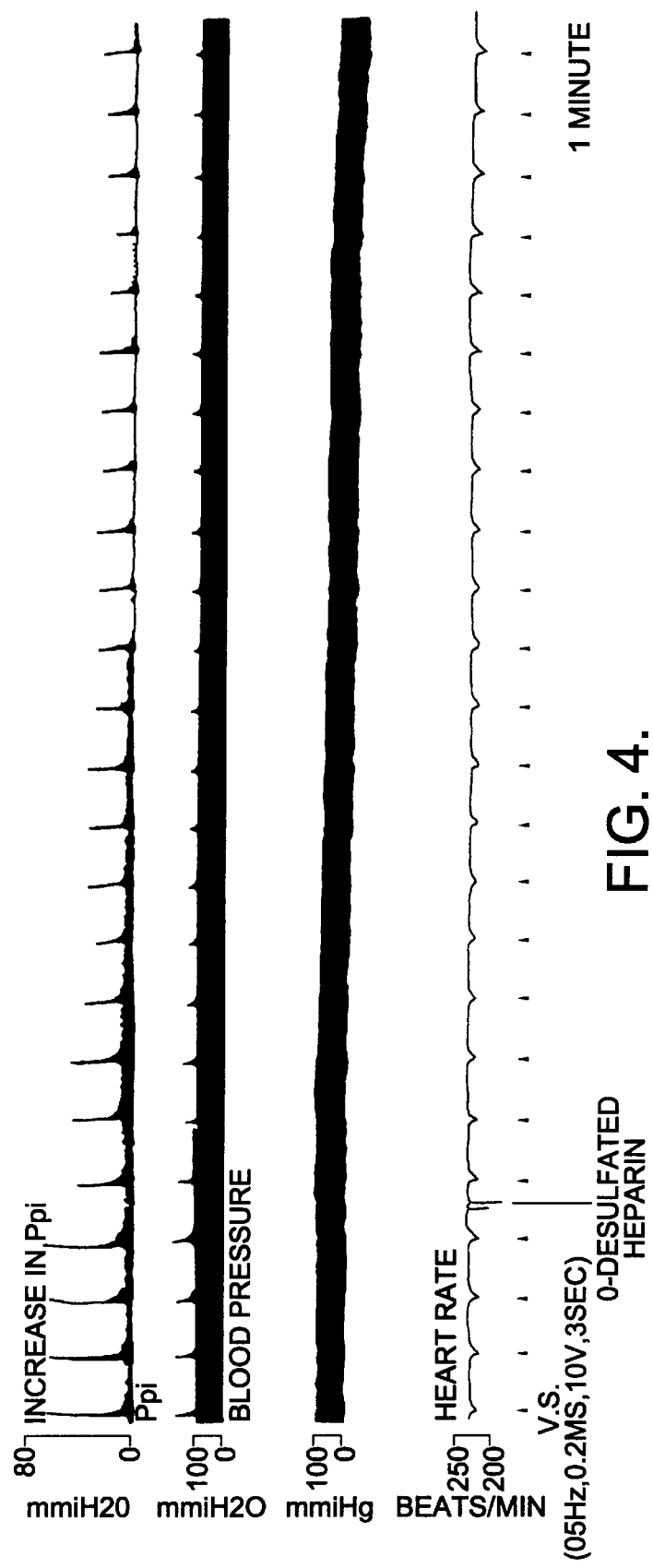

FIG. 4 shows the inhibition of vagally-induced bronchoconstriction by O-desulfated heparin in sensitized guinea-pigs challenged with ovalbumin.

Figure 5:
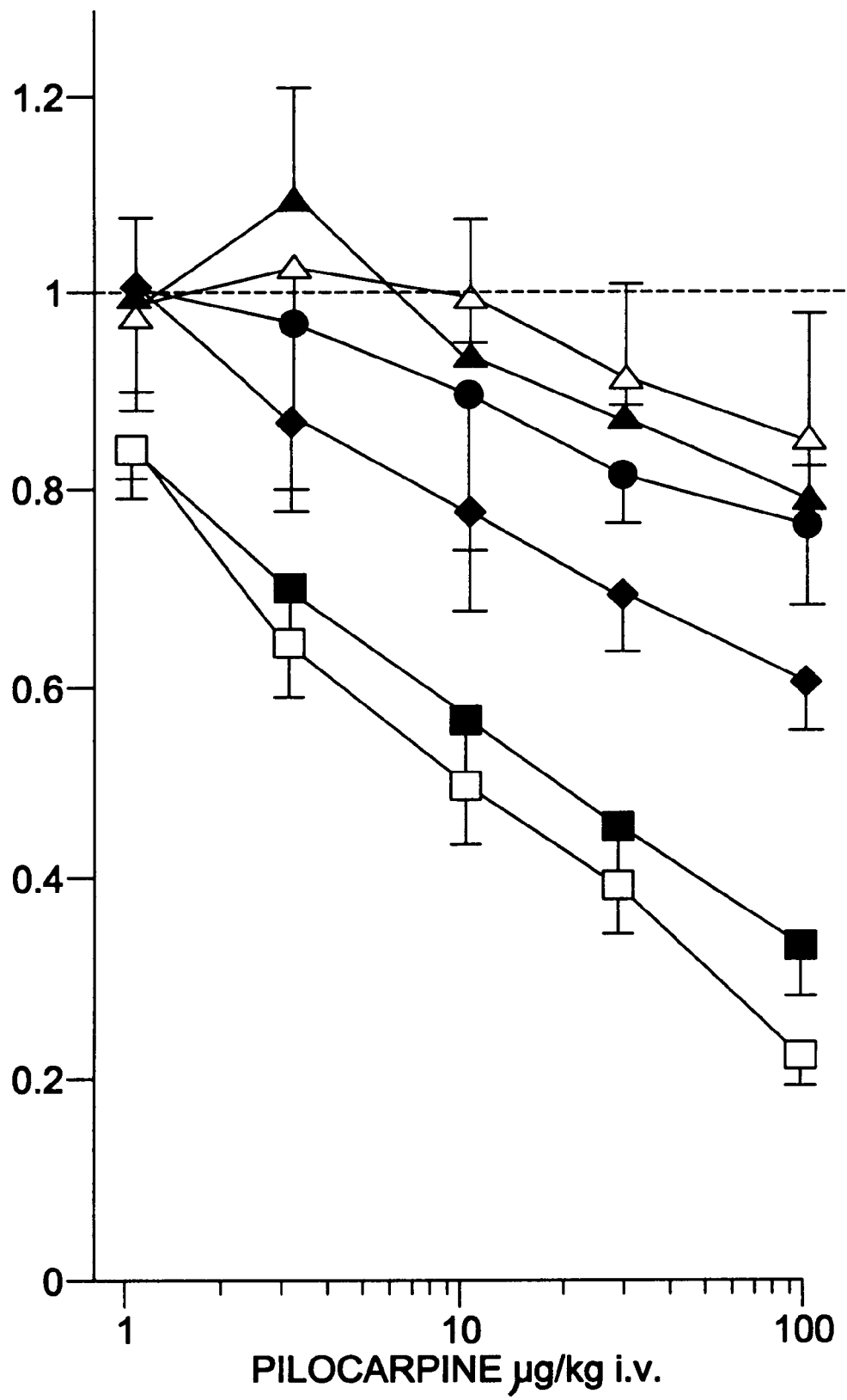

FIG. 5 shows a graph of the effect of heparin and O-desulfated heparin on the response to pilocarpine in antigen challenged guinea-pigs. Results are expressed as the ratio of vagally-induced bronchoconstriction after pilocarpine to vagally-induced bronchoconstriction before pilocarpine. Each point is the mean of 4-6 animals with s.e. mean shown by vertical bars. Pilocarpine (1-100 µg/kg iv) significantly inhibited vagally-induced bronchoconstriction in control guinea-pigs (open squares, P=0.01). Following antigen challenge the effect of pilocarpine on vagally-induced bronchoconstriction was abolished (open triangles). The effect of pilocarpine on vagally-induced bronchoconstriction was restored in a dose dependent manner by administration of O-desulfated heparin (11.4 mg/kg, closed triangles; 22.8 mg/kg, closed circles; 57.0 mg/kg, closed diamonds; 91.2 mg/kg, closed squares). *Significantly different from control; +significantly different from antigen challenged (open triangles), using two way analysis of variance for repeated measures.

Figure 6:
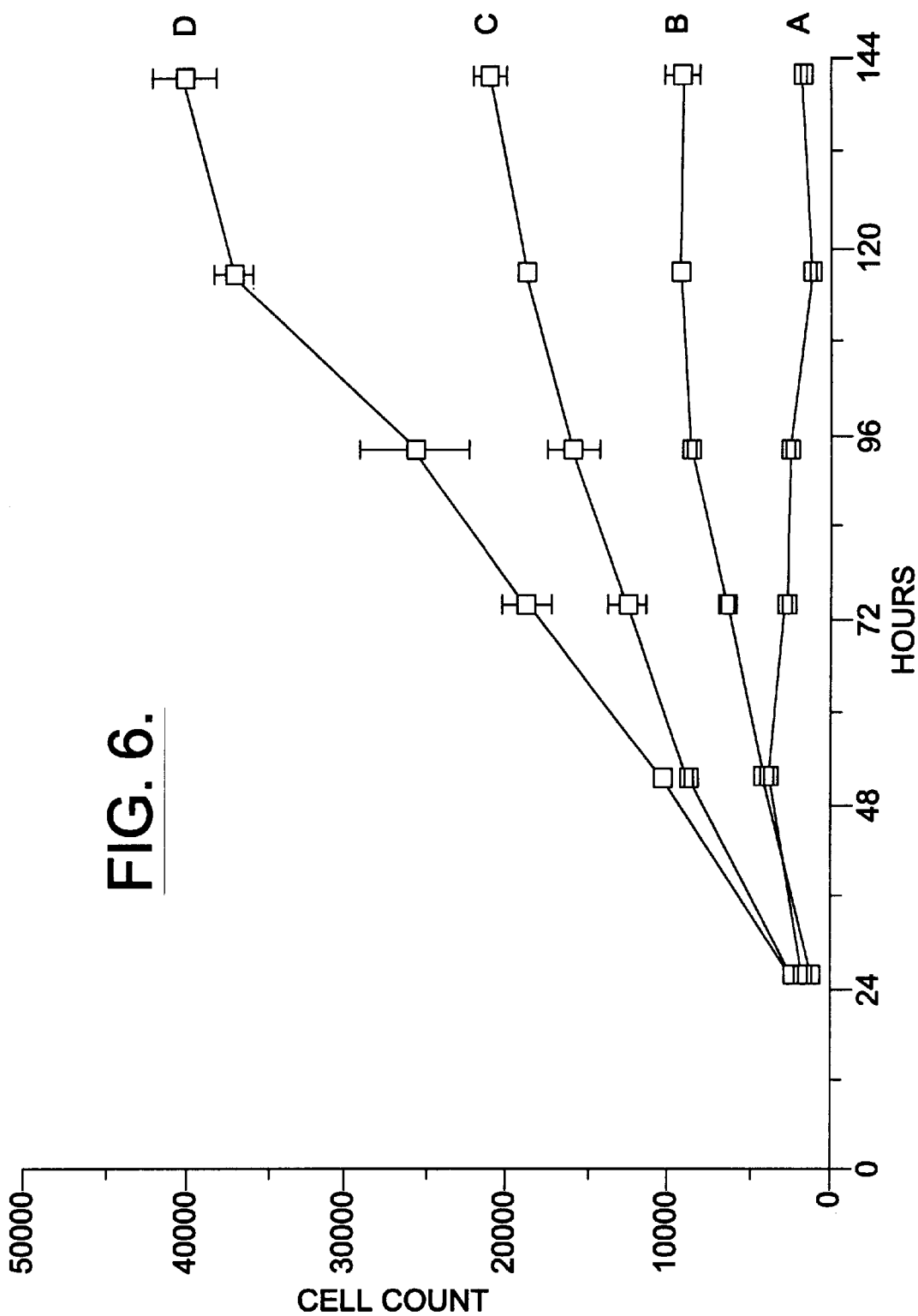

FIG. 6 shows a graph of the effect of serum on airway smooth muscle cell proliferation. Cells were exposed to serum, cell counts were performed at 24 hour intervals, and results are expressed as cell count in each of four concentrations of serum at each 24 hour interval. The serum concentrations are as follows: (A) 0.25% FBS; (b) 2.5% FBS; (C) 5.0% FBS; and (D) 10.0% FBS. Each point represents the mean plus standard error of cell counts in at least 5 wells.

Figure 7:
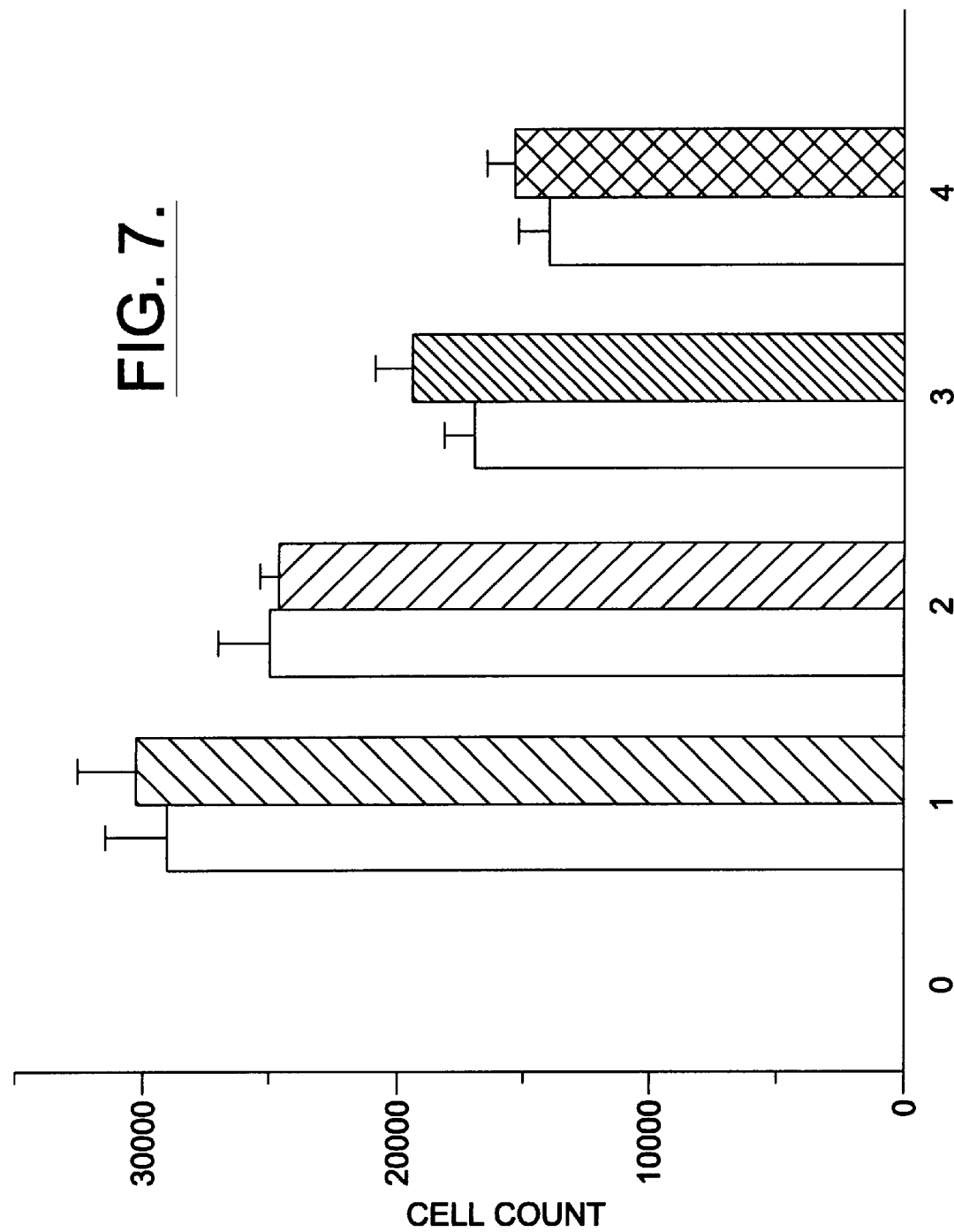

FIG. 7 shows a bar graph of the effect of heparin and O-desulfated heparin on airway smooth muscle cells. Solid bars indicate heparin and hatched bars indicate O-desulfated heparin. Concentrations added to the cells are as follows: (1) 0 µg/ml, (2) 2.0 µg/ml, (3) 20 µg/ml, (4) 200 µg/ml. Cell counts were performed after 62 hours of incubation with the indicated compound. Each bar represents the mean plus standard error in cells in at least 5 wells.

Figure 8:
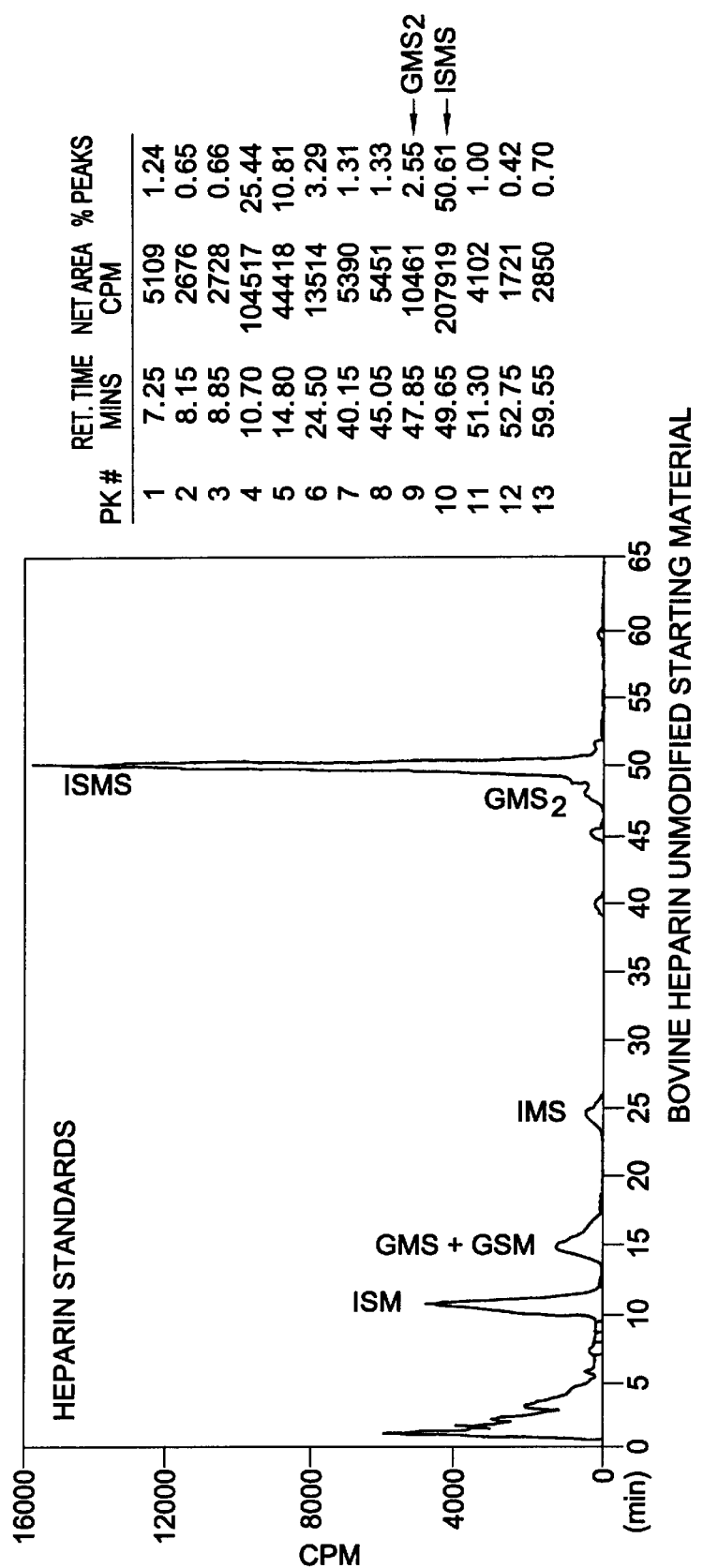

FIG. 8 shows the spectra of bovine heparin unmodified starting material.

Figure 9:
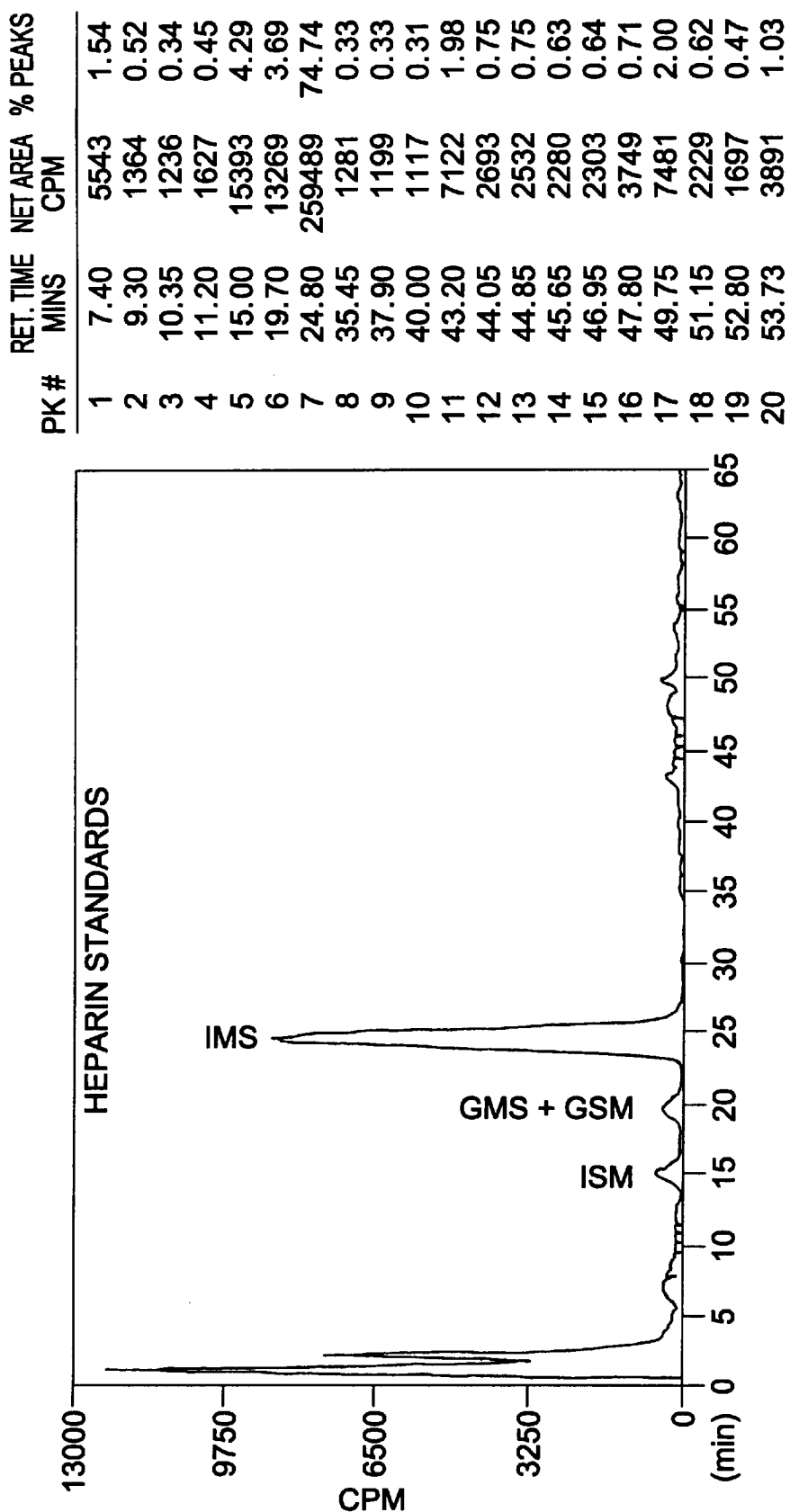

FIG. 9 shows the spectra of O-desulfated bovine heparin of the invention.

Figure 10:
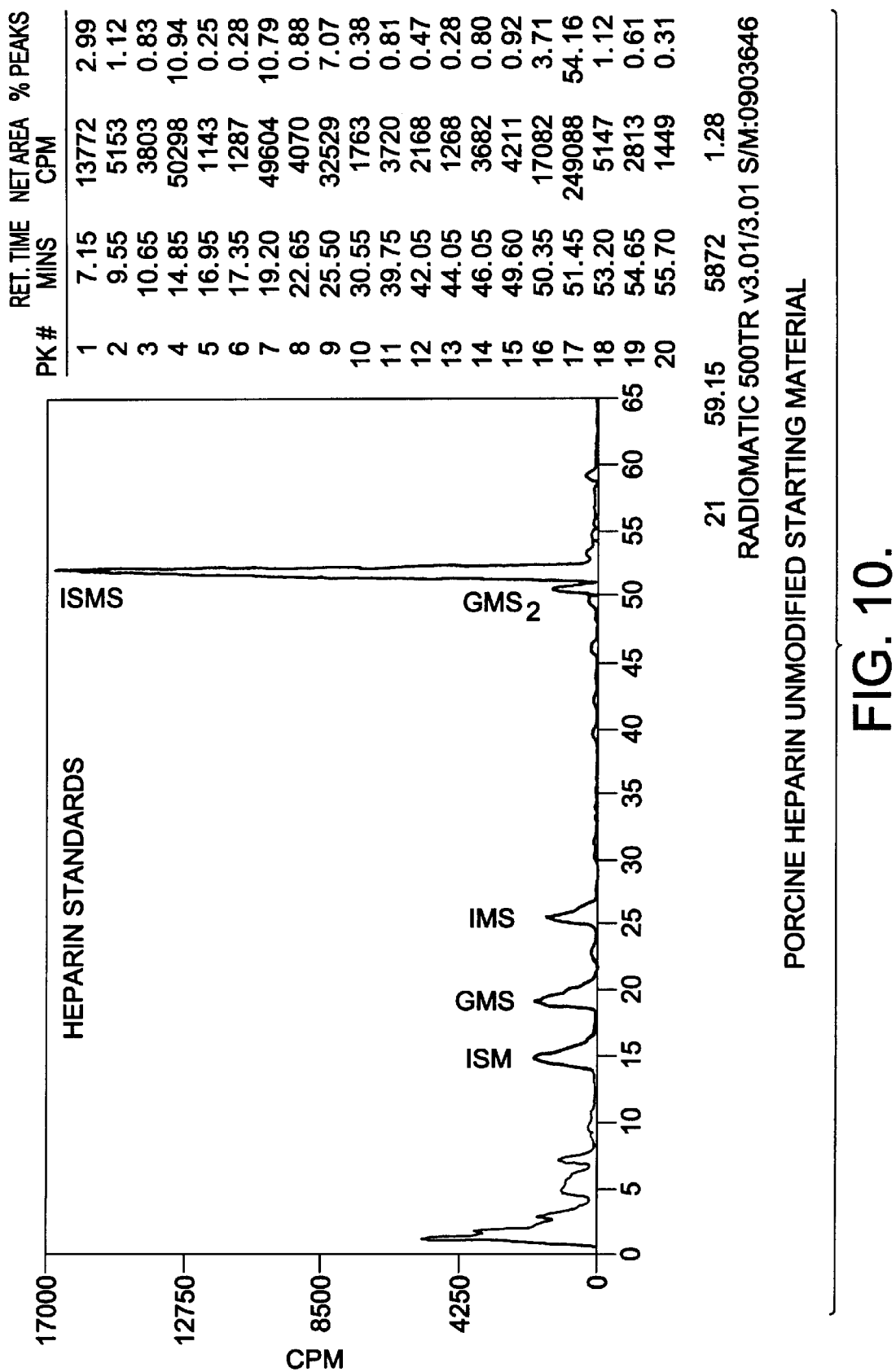

FIG. 10 shows the spectra of porcine heparin unmodified starting material.

Figure 11:
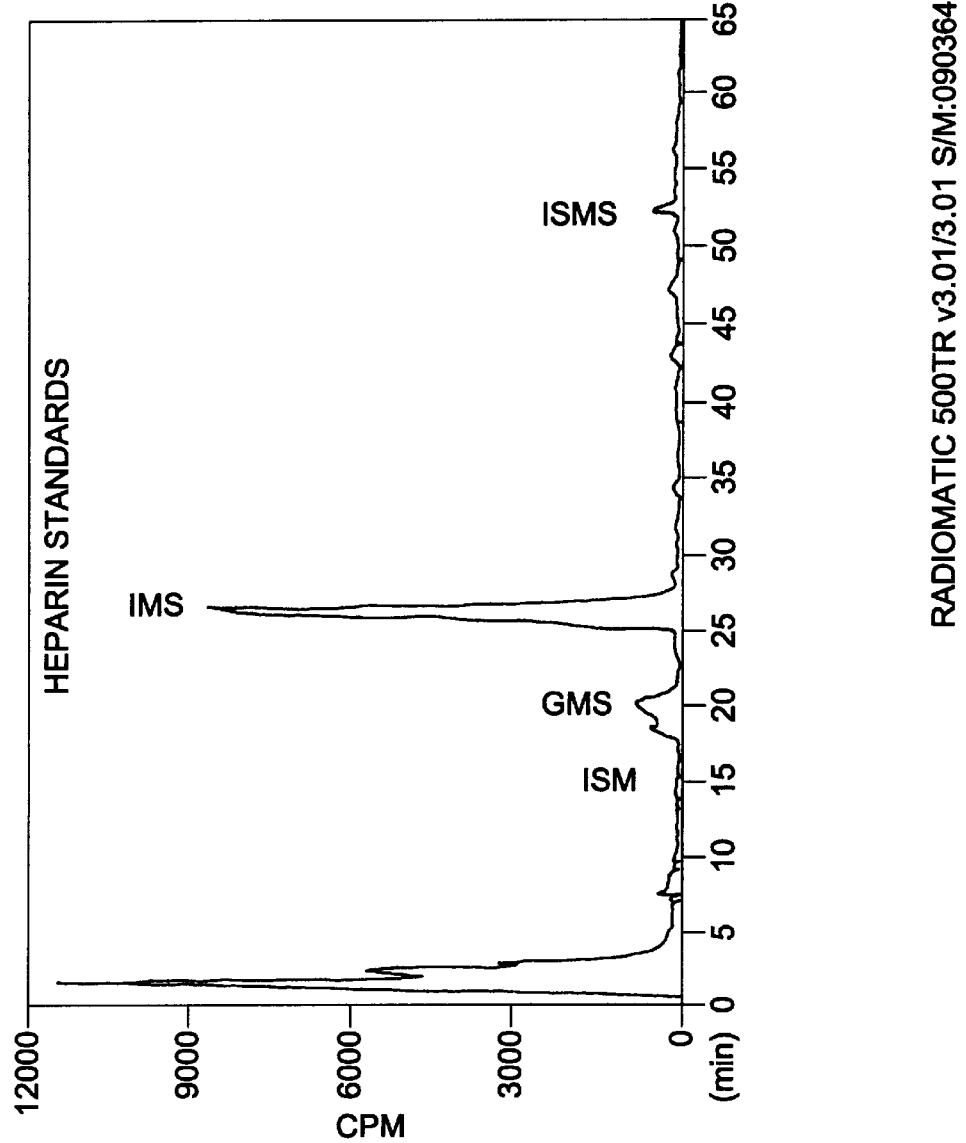

FIG. 11 shows the spectra of O-desulfated porcine heparin of the invention.

DETAILED DESCRIPTION OF THE INVENTION

The present invention may be understood more readily by reference to the following detailed description of specific embodiments and the Examples and Figures included therein.

As used in the claims, "a" can mean one or more, depending upon the context in which it is used.

The present invention provides a method of treating and preventing asthmatic reactions. These reactions can be treated and prevented in subjects having intrinsic asthma, i.e., having chronic, low level inflammation in the airways which additionally can flare up into airways hyperreactivity in response to an irritant. These reactions can be treated and prevented in subjects having extrinsic asthma, i.e., having chronic inflammation in the airways that further responds by airways hyperreactivity to exposure to an antigen. By "airways hyperreactivity" or "airways hyperresponsiveness," as used herein, is meant a hyperacute response in the airways that is above the normal, non-asthmatic person's response to any stimulus, i.e., antigen or irritant. This response can include increased release of acetylcholine, influx of inflammatory cells such as eosinophils and concomitant release of positively charged proteins (including major basic protein, eosinophil peroxidase and eosinophil cationic protein), airway inflammation, and bronchoconstriction.

The present invention provides a method of reducing asthmatic response in a mammal, comprising administering an asthmatic response-reducing amount of O-desulfated heparin to the subject, thereby reducing asthmatic response in the mammal. By "asthmatic response" in included any physiological response in the airway associated with asthma, such as airways hyperreactivity, bronchoconstriction, desensitization of $M_2$ muscarinic receptor, and proliferation of airway smooth muscle cells.

Specifically, the present invention provides a method for reducing airways hyperreactivity of an asthmatic response in a mammal comprising administering to the mammal an airways hyperreactivity-reducing amount of O-desulfated heparin having O-desulfation at least at the 2-O and 3-O positions, thereby reducing the airways hyperreactivity in the mammal.

The present invention further provides a method for increasing activity of a desensitized $M_2$ muscarinic receptor in an asthmatic mammal comprising administering to the mammal an activity-increasing, amount of O-desulfated heparin having O-desulfation at least at the 2-O and 3-O positions, thereby increasing the $M_2$ muscarinic receptor activity in the mammal.

The present invention additionally provides a method for reducing bronchoconstriction in a mammal comprising administering to the mammal a bronchoconstriction-reducing amount of O-desulfated heparin having O-desulfation at least at the 2-O and 3-O positions, thereby reducing the bronchoconstriction in the mammal.

The present invention further provides a method for reducing airway smooth muscle cell proliferation in a mammal comprising administering to the mammal an airway smooth muscle cell proliferation-reducing amount of O-desulfated heparin having O-desulfation at least at the 2-O and 3-O positions, thereby reducing the airway smooth muscle cell proliferation in the mammal.

The present invention further provides a method for inhibiting complement-mediated hemolysis in a mammal comprising administering to the mammal a complement-mediated hemolysis-inhibiting amount of O-desulfated heparin having O-desulfation at least at the 2-O and 3-O positions, thereby inhibiting complement-mediated hemolysis in the mammal. Inhibiting complement-mediated hemolysis can comprise reducing complement-mediated hemolysis relative to complement-mediated hemolysis in the absence of an inhibitor of complement-mediated hemolysis.

By "O-desulfated heparin" is meant that the heparin is O-desulfated sufficiently to have resulted in any reduction of the anticoagulant activity of the heparin. O-desulfated heparin includes heparin prepared by the process described in Example I to be at least partially, and preferably substantially, desulfated at least at the 2-O position and at the 3-O position. Preferably, the O-desulfated heparin is at least about 10%, more preferably at least about 25%, more preferably at least about 40%, more preferably at least about 50%, more preferably at least about 60%, more preferably at least about 75%, more preferably at least about 80%, more preferably at least about 90%, more preferably at least about 95%, more preferably at least about 97% and more preferably at least about 98%, or 100% desulfated, independently, at each of the 2-O position and the 3-O position, as determined by disaccharide analysis. Extent of desulfation need not be the same at each O-position. Extent of O-desulfation can be determined by known methods such as disaccharide analysis. Desulfation at the 6-O position can not be determined by currently available techniques. In a preferred embodiment, the 6-O position is substantially sulfated although it can not be determined if some, particularly a minor amount, of the sulfates were lost (desulfated) during the preparation of the compounds used in the present invention. Desulfation at the N-position is not expected to occur to any appreciable extent under the conditions described. A method of preparing O-desulfated heparin is set forth in the examples. O-desulfated heparin is effective in reducing the $M_2$ muscarinic receptor blockade contributing to exaggerated airways reactivity of asthma, but without the anticoagulating properties of untreated heparin. Administering O-desulfated heparin also includes that the O-desulfated heparin is in a pharmaceutically acceptable state, e.g., that it is sufficiently neutral in pH to administer, as is known in the art. One in the art will know how to adjust the pH to be in an acceptable range and will know a pharmaceutically acceptable range. Preferably the pH is between about 6 and about 7 for an aerosol preparation and about 7 to about 7.5 for intravenous administration to be considered acceptable. To neutralize an alkaline pH, typically the solution is ultrafiltrated with large volumes of water, the pH brought back to a neutral pH with any selected acid such as hydrochloric acid, and then the solution is dried, lyophilized or vacuum distilled.

"O-desulfated heparin" can include O-desulfated heparin having modifications, such as reduced molecular weight or acetylation, deacetylation, oxidation, and decarboxylation, as long as it retains its ability to restore abnormal $M_2$ receptor function and to inhibit exaggerated airways reactivity of asthma. The modified O-desulfated heparin can be readily assessed for these activities utilizing known methods, given the teachings herein. Such modifications can be made either prior to or after partial desulfation and methods for modification are standard in the art. Several low molecular weight modifications of heparin have been developed (see page 581, Table 27.1 Heparin, Lane & Lindall). The molecular weight typically can range from about 2500 to about 8100, and O-desulfated heparin having reduced molecular weight retaining asthma response-reducing function can also be utilized. Low molecular weight heparins can also be made enzymatically by utilizing heparinase enzymes to cleave heparin into smaller fragments. Such reduced molecular weight O-desulfated heparin can typically have a molecular weight of from about 1000 to about 8000.

For example, periodate oxidation (U.S. Pat. No. 5,250,519, Conrad and Yuchuan) is a known oxidation method that produces an oxidized heparin having reduced anticoagulant activity. Other oxidation methods, also well known in the art, can be used. Additionally, for example, decarboxylation of heparin is also known to decrease anticoagulant activity, and such methods are standard in the art. Furthermore, low molecular weight heparins are known in the art to have decreased anti-coagulant activity, and they are produced by standard techniques. Thus, modified O-desulfated heparin contemplated for use in the present invention can include, for example, periodate-oxidized O-desulfated heparin, decarboxylated O-desulfated heparin, acetylated O-desulfated heparin, deacetylated O-desulfated heparin, deacetylated, oxidized O-desulfated heparin and low molecular weight O-desulfated heparin. Many other modifications will be apparent to those of skill in the art, given the teachings provided herein.

By "reducing" or "increasing" a response or activity is meant that the response or activity is reduced or increased relative to the level of response in the subject prior to the administration of the O-desulfated heparin. Typically, such reduction or increase can be readily ascertained by the subject by experiencing a reduction in the symptoms of the asthmatic response, e.g., relief in breathing. "Reducing" or "increasing" a response or activity also means reducing or increasing a response relative to a typical level of response for that subject in the absence of treatment. Additionally, an increase or reduction can readily be determined according to the teachings herein and standard methods in the art by measuring a relevant parameter prior to administration and then measuring it again after administration. Additionally, standard doses can be initially determined, even for a particular subject, and then routinely administered for a routine treatment.

An asthmatic response-reducing amount of O-desulfated heparin is an amount that causes a reduction in any of the responses of an asthmatic episode, such as airways hyperreactivity, bronchoconstriction, and proliferation of airway smooth muscle cells. An "airways hyperreactivity-reducing amount" is an amount that causes a reduction in any of the manifestations of airways hyperreactivity, such as an amount that causes an increase in impaired $M_2$ receptor activity in asthmatics, an amount that reduces inflammation, and/or an amount that decreases bronchoconstriction. A desensitized $M_2$ muscarinic receptor "activity-increasing amount" is an amount that causes an increase in activity of a desensitized $M_2$ muscarinic receptor in an asthmatic. A "bronchoconstriction-reducing amount" is an amount that reduces the bronchoconstriction response in an asthmatic. An "airways smooth muscle cell proliferation-reducing amount" is an amount that reduces airway smooth muscle cell proliferation in an asthmatic response. A "complement-mediated hemolysis-inhibiting amount" is an amount that reduces or inhibits complement-mediated hemolysis in a subject, particularly in an asthmatic subject. Any effective dose is an amount sufficient to bind and thus neutralize the positive charge on the positively-charged proteins released into the airways in airways hyperreactivity. An effective amount can vary for the specific individual and can be tailored according to the severity of the reaction. For example, one can administer a higher dosage for a more severe reaction and a lower dose for a less severe reaction. Additionally, administration can be repeated, with the same or an adjusted amount, if sufficient relief is not obtained from the initial dose. Thus, a conservative dose can be initially administered, and if relief is not obtained, further dose(s) can be administered as necessary for relief.

For example, an effective dose can be a dose greater than about 1 mg/kg, and preferably greater than about 5 mg/kg, more preferably greater than about 10 mg/kg, and further, the effective dose is preferably less than about 100 mg/kg, and preferably less than about 70 mg/kg. A preferable dose range can be from about 1 mg/kg to about 70 mg/kg. Another preferable dose range can be from about 50 mg to about 500 mg. Thus a typical minimal dose can comprise about 50 mg and a typical maximal dose can comprise about 5.0 grams of O-desulfated heparin for an average human adult.

The present invention further provides a method for preventing airways hyperreactivity in a mammal comprising administering to the mammal an airways hyperreactivity-reducing amount of O-desulfated heparin having O-desulfation at least at the 2-O and 3-O positions, thereby preventing the airways hyperreactivity in the mammal. The invention additionally provides a method for preventing bronchoconstriction in a mammal comprising administering to the mammal a bronchoconstriction-reducing amount of O-desulfated heparin having O-desulfation at least at the 2-O and 3-O positions, thereby preventing the bronchoconstriction in the mammal. Further, the invention provides a method of preventing airway smooth muscle cell proliferation in a mammal comprising administering to the mammal an airway smooth muscle cell proliferation-inhibiting amount of O-desulfated heparin having O-desulfation at least at the 2-O and 3-O positions, thereby preventing airway smooth muscle cell proliferation.

By "prevention" is meant that the asthmatic response does not reach an acute level and is substantially not detectable. For prevention, the O-desulfated heparin can be administered prior to exposure to an antigen, such as prior to a predicted contact with a known antigen. Also, the O-desulfated heparin can be administered on a routine basis to continually prevent airways hyperreactivity and/or airway smooth muscle cell proliferation. Asthma is well-suited for prevention of airways hyperreactivity and/or bronchoconstriction because of the constant low level of inflammation. Prevention involves a continual binding of positive charges in the airways by the negatively charged O-desulfated heparin.

Preferably a prevention method of this invention comprises a constant suppression of the asthmatic response, which can be achieved by a repetitive, routine administration of the O-desulfated heparin. With repetitive, routine administration, an optimal dose can readily be ascertained by varying the dose until the optimal prevention is achieved. Preferably, the dose is administered about 2–4 times per day.

Additionally, upon exposure to large amounts of an antigen or irritant, if eventually a response occurs, an additional dose of O-desulfated heparin can be administered. Additionally, when an exposure to a large antigen amount is known in advance, an additional dose of O-desulfated heparin can be administered to prevent a response. Because the dose of O-desulfated heparin needed to reduce or prevent a response to an antigen is directly related to the amount of positive charge in the airway, brought in by the migration of cells having positively charged proteins resulting from the exposure to the antigen or irritant, to be bound by the negatively charged heparin, one can readily determine when additional doses may be necessary and determine an appropriate amount. A typical dose for repetitive, preventive administration can be from about 0.5 mg/kg to about 70 mg/kg, with a preferable dose being from about 5 mg/kg to about 7 mg/kg. This preferable dose can be given as often as necessary to prevent the response.

The present invention further provides a method for reducing airways hyperreactivity of an asthmatic response in a mammal comprising administering to the mammal an airways hyperreactivity-reducing amount of O-desulfated heparin, wherein the O-desulfated heparin is made by a process comprising alkalinizing a solution containing reduced heparin to pH 13 or greater and allowing desulfation to occur, thereby reducing the airways hyperreactivity in the mammal. Desulfation can be accomplished faster by lyophilizing, drying or vacuum distilling the alkaline heparin solution. The extent of desulfation can be determined during the desulfation process by removing a sample and determining the extent of desulfation of the sample by standard means such as disaccharide analysis. The alkaline solution should be neutralized prior to administration, which can be accomplished by ultrafiltration with large volumes of water, adjusting the pH to neutral pH by standard procedures, such as addition of hydrochloric acid, followed by lyophilizing, drying or vacuum distilling. Similarly, the present invention provides a method for increasing activity of a desensitized $M_2$ muscarinic receptor in an asthmatic mammal comprising administering to the mammal an activity-increasing amount of O-desulfated heparin made by the present process. Additionally, the present invention provides a method for reducing bronchoconstriction in a mammal comprising administering to the mammal a bronchoconstriction-reducing amount of O-desulfated heparin made by the present process. Further, the present invention provides a method for reducing airway smooth muscle cell proliferation comprising administering to the mammal an airway smooth muscle cell proliferation-reducing amount of O-desulfated heparin made by the present process. Additionally provided by the present invention is a method for inhibiting complement-mediated hemolysis in a mammal comprising administering to the mammal a complement-mediated hemolysis-inhibiting amount of O-desulfated heparin made by the present process. An example of the present process is provided in Example I, which demonstrates the more rapid desulfation process achieved by lyophilizing the alkaline heparin solution. Alternatively, the alkaline heparin solution can be dried or vacuum distilled or simply allowed to stand to proceed with desulfation.

Heparin dissolution can be at about 1–10% concentration of heparin. If desired, heparin can be optionally treated for molecular weight control (reducing the amount of fragmentation of the heparin) with a reducing agent, such as, but not limited to, sodium borohydride, catalytic hydrogen, and lithium aluminum hydride, which can be added in the conventional manner of alkalinizing the solution slightly to pH 8–9 with sodium bicarbonate (Conrad, et el., U.S Pat. No. 5,250,519 (Oct. 5, 1993)), but the reducing agent, if used, can preferably be added without slightly alkalinizing the solution (i.e., without sodium bicarbonate). The solution can be incubated with the reducing agent for about 12–24 hours at about 15–30° C., or more preferably, about 20–25° C. The time of incubation need only be sufficiently long for reduction of the heparin to occur, such as from about 4 hours, and can extend to over several days, such as greater than 60 hours. After this incubation, a base, such as sodium hydroxide, is added to raise the pH to 13 or greater, preferably to a concentration of about 0.25 to 0.50 M. This alkaline solution can then be dried, lyophilized or vacuum distilled. These processes can speed up the O-desulfation process; alternatively, the solution can be allowed to proceed with O-desulfation without utilizing these processes. Regardless of the specific such process used, the heparin is then neutralized prior to administration to a pharmaceutically acceptable pH. Typically, the O-desulfated heparin is neutralized by ultrafiltration with large volumes of water and, if necessary, the pH is adjusted by standard means such as the addition of hydrochloric acid, and the O-desulfated heparin is then dried, lyophilized or vacuum distilled. Methods of preparation of O-desulfated heparin as used herein are disclosed in WO 95/21198 published Aug. 10, 1995, the disclosure of which is hereby incorporated by reference in its entirety.

The instant medicaments can further comprise the O-desulfated heparin, or modification thereof, in a physiologically acceptable carrier for administration. Any physiologically acceptable carrier can be utilized, such as physiologically buffered saline, normal saline and distilled water. By "pharmaceutically acceptable" is meant a material that is not biologically or otherwise undesirable, i.e., the material may be administered to an individual along with the O-desulfated heparin without causing any undesirable biological effects or interacting in a deleterious manner with any of the other components of the pharmaceutical composition in which it is contained.

The invention provides that the O-desulfated heparin can be administered in aerosol particles, by inhalation, by intratracheal injection, by intravenous (iv) injection, by peritoneal injection, or orally. Such administrations can comprise a physiologically acceptable carrier and an effective amount of O-desulfated heparin or analog thereof Aerosol particles can consist essentially of particles less than 10 microns and preferably less than 5 microns. Such aerosols can be provided by available jet aerosol or ultrasonic nebulizer systems in common use, or by dry powder inhalation systems known in the art.

Depending on the intended mode of administration, the pharmaceutical compositions may be in the form of solid, semi-solid, or liquid dosage forms, such as, for example, a dry powder or a liquid for aerosol inhalation. The compositions will include, as noted above, an effective amount of the selected drug in combination with a pharmaceutically acceptable carrier and, in addition, may include other medicinal agents, pharmaceutical agents, carriers, adjuvants, diluents, etc. Compounds can be administered, e.g., as a complex with cationic liposomes, or encapsulated in anionic liposomes.

Liquid pharmaceutically administrable compositions can, for example, be prepared by dissolving, dispersing, etc. an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Liquid compositions can be aerosolized for administration. Actual methods of preparing such dosage forms are known, or will be apparent, to those skilled in this art; for example, see Remington's *Pharmaceutical Sciences*, E. W. Martin, (ed.), Mack Publishing Co., Easton, Pa.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

The present invention is more particularly described in the following examples which are intended as illustrative only, since numerous modifications and variations therein will be apparent to those skilled in the art.

EXAMPLES

Example I

O-Desulfation of Heparin

A 5% aqueous solution of porcine intestinal mucosal sodium heparin (Scientific Protein Labs, Waunakee, Wis.) was made by adding 500 gm heparin to 10 L deionized water. Sodium borohydride was added to 1% final concentration and the mixture was incubated overnight at 25 degrees C. Sodium hydroxide was then added to 0.4 M final concentration (pH at least 13) and the mixture was frozen and lyophilized to dryness. Excess sodium borohydride and sodium hydroxide were removed by ultrafiltration. The final product was adjusted to pH 7.0, precipitated by addition of three volumes of cold ethanol and dried. The O-desulfated heparin produced by this procedure was a fine crystalline slightly off-white powder with less than 10 USP units/mg anti-coagulant activity and less than 10 U/mg anti-Xa anti-coagulant activity.

The synthesis of O-desulfated heparin by reducing heparin in solution and drying, lyophilizing, or vacuum distilling the reduced heparin solution can include the following modifications. One can place the starting heparin in, for example, water, or other solvent, as long as the solution is not highly alkaline. A typical concentration of heparin solution can be from 1 to 10 percent heparin. The heparin used in the reaction can be obtained from numerous sources, known in the art, such as porcine intestine or beef lung. One can utilize heparin that has been modified in any of a number of ways known to those of skill in the art, discussed above.

The reduced heparin solution can be dried, lyophilized or the solvent can be vacuum distilled. Lyophilization or vacuum distillation of the solvent is preferred. Generally, lyophilization is utilized. The heparin can be reduced by incubating it with a reducing agent, such a sodium borohydride, catalytic hydrogen, or lithium aluminum hydride. A preferred reduction of heparin is performed by incubating the heparin with sodium borohydride. Generally, about 10 grams of $NaBH_4$ can be used per liter of solution, but this amount can be varied as long as reduction of the heparin occurs. Additionally, other known reducing agents can be utilized but are not necessary for producing a treatment effective O-desulfated heparin. The incubation can be achieved over a wide range of temperatures, taking care that the temperature is not so high that the heparin caramelizes. A suggested temperature range is about 15–30 degrees C., or even about 20–25 degrees C. The length of the incubation can also vary over a wide range, as long as it is sufficient for reduction to occur. For example, several hours to overnight (i.e., about 4 to 12 hours) can be sufficient. However, the time can be extended to over several days, for example, exceeding about 60 hours.

Additionally, the method of synthesis can be adapted by raising the pH of the reduced solution to 13 or greater by adding a base capable of raising the pH to 13 or greater to the reduced heparin solution. The pH can be raised by adding any of a number of agents including hydroxides, such as sodium, potassium or barium hydroxide. A preferred agent is sodium hydroxide (NaOH). Even once a pH of 13 or greater has been achieved, it can be beneficial to further increase the concentration of the base. For example, it is preferable to add NaOH to a concentration of about 0.25 M to about 0.5 M NaOH. This alkaline solution is then dried, lyophilized or vacuum distilled.

Example II
Analysis of Extent of 2-O- and 3-O-desulfation of O-desulfated Heparin The following two sets of disaccharide analyses, on bovine and on porcine-derived samples, were performed, the commensurate disaccharide analysis HPLC spectras were produced and the quantitative integration and identification of the HPLC peaks was done to determine the degree of desulfation of the four heparin samples.

Disaccharide analysis was performed by the method of Guo and Conrad (Guo, Y., and H. E. Conrad. 1988. Analysis of oligosaccharides from heparin by reversed-phase ion-pairing high-performance liquid chromatography. *Anal. Biochem.* 178:54–62). In this process N-acetyl-D-glucosamine residues are deacylated with hydrazine. The heparin is then deaminated and depolymerized by exposure to nitrous acid at pH 4 to break bonds between D-glucosamine and uronic acids, and then at pH 1.5 to break bonds between D-glucosamine N-sulfate and uronic acids. Both reactions leave O-sulfates intact, and convert glucosamine or glucsamine-N-sulfate to anhydromannose, which is radiolabeled with $NaB[^3H_4]$, converting anhydromannose to anhydromannitol. Radiolabeled disaccharides are then separated by reverse-phase, ion-pairing high pressure liquid chromatography.

The first set of analyses was performed on bovine lung heparin comparing: a) the starting material, bovine lung heparin obtained from Sigma Chemical Corp. (FIG. 8) and b) the product, O-desulfated bovine lung heparin produced by adding 160 mg of the starting bovine lung heparin to 40 ml deionized water to make a 0.4% solution, adjusting the solution to pH 13 or greater with sodium hydroxide, freezing, and lyophilizing the material as presented in Example I (FIG. 9).

The results of the first comparison show that the first product, O-desulfated bovine lung heparin, is about 97.6% 2-O desulfated and about 99% 3-O desulfated, relative to the first starting material. Desulfation at the 2-O position can be detected because in the starting material, the ISM peak at 10.7 min. has an area of 104,517 cpm, and the ISMS peak at 49.65 min. has an area of 207,919 cpm, whereas the product has a negligible ISM peak and an ISMS peak at 49.75 min. of 7,461 cpm, representing about a 97.6% reduction in 2-O sulfate groups. Desulfation at the 3-O position can be detected because in the starting material, the $GMS_2$ peak at 47.85 min. has an area of 10,461 cpm, whereas the product has a negligible $GMS_2$ peak, representing about 99% reduction in 3-O sulfate groups. (See FIG. 8 and FIG. 9) The first product was still substantially sulfated at the 6-O position relative to the starting material, as evidenced by a large IMS peak in the first product.

The second set of analyses was performed on porcine mucosal heparin comparing: a) the starting material, porcine mucosal heparin obtained from Sigma Chemical Corp. (FIG. 10) and b) the product, O-desulfated porcine mucosal heparin produced by adding 160 mg of the starting porcine mucosal heparin to 40 ml deionized water to make a 0.4% solution, adjusting the solution to pH 13 or greater with sodium hydroxide, freezing, and lyophilizing the material as presented in Example I (FIG. 11).

The results of the second comparison show that the second product, O-desulfated porcine mucosal heparin, is about 97.1% 2-O desulfated and about 99% 3-O desulfated, relative to the second starting material. Desulfation at the 2-O position can be detected because in the starting material, the ISM peak at 14.85 min. has an area of 50,298 cpm, and the ISMS peak at 51.45 min. has an area of 249,088 cpm, whereas the product has a negligible ISM peak and an ISMS peak at 52.15 min. of 8,471 cpm, representing about a 97.1% reduction in 2-O sulfate groups. Desulfation at the 3-O position can be detected because in the starting material, the $GMS_2$ peak at 50.35 min. has an area of 17,082 cpm, whereas the product has a negligible $GMS_2$ peak, representing about 99% reduction in 3-O sulfate groups. The second product was still substantially sulfated at the 6-O position relative to the starting material, as evidenced by a large IMS peak in the second product.

Figure 1:
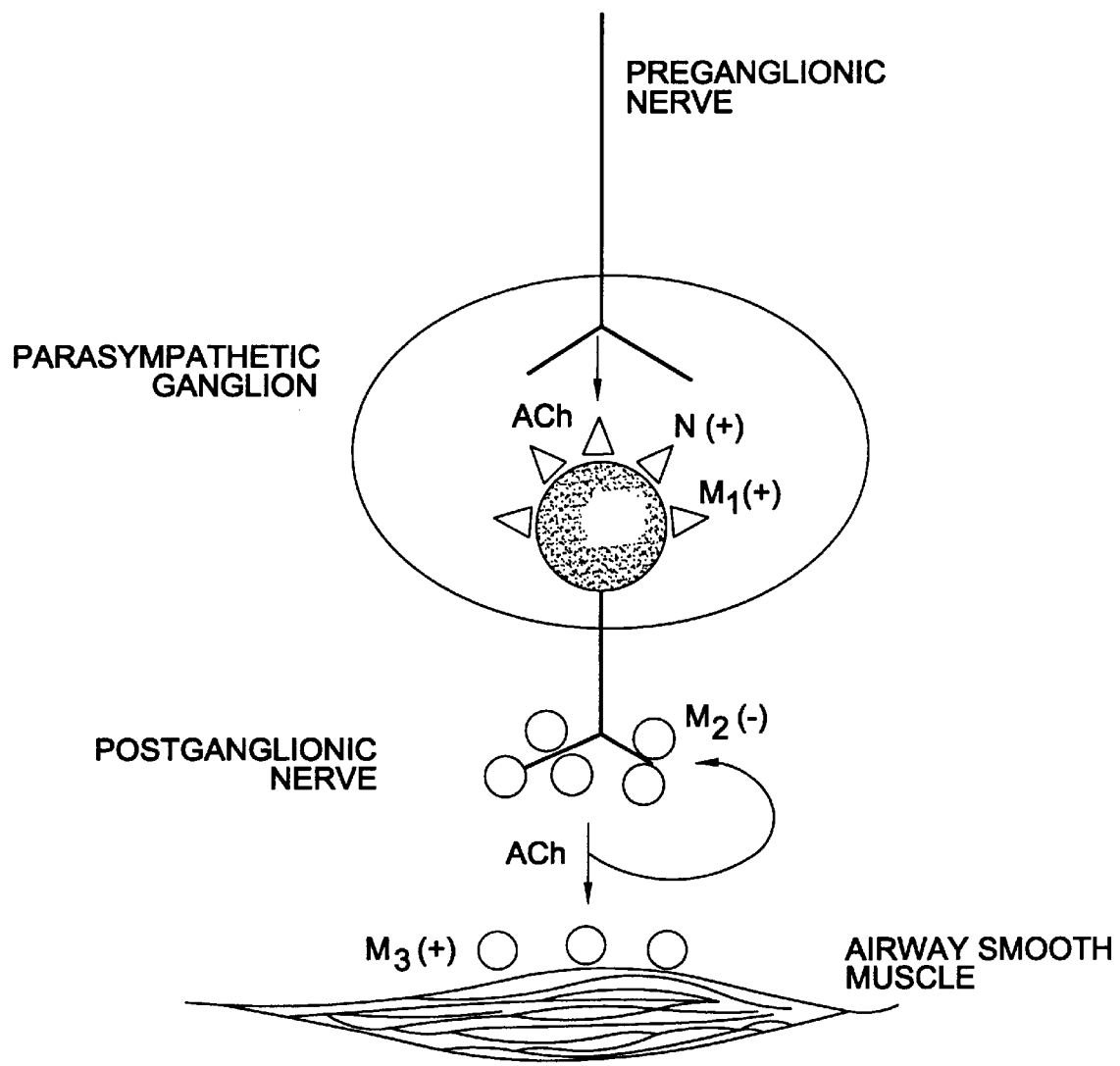
FIG. 1 shows a schematic drawing of cholinergic neural pathways and muscarinic receptor subtypes of the afferent sensory and efferent motor limbs of the vagus nerve innervation of the lung airway. Abbreviations are as follows.

Example III
Treatment of Asthmatic Airways Hyperreactivity by O-Desulfated Heparin In the lungs the release of acetylcholine from the vagus nerves is under the local control of inhibitory muscarinic autoreceptors on the post-ganglionic nerves, as shown in FIG. 1. These $M_2$ autoreceptors provide negative feedback control of acetylcholine release. This negative feedback control can be demonstrated in vivo by measuring vagally-induced bronchoconstriction in the presence of the selective $M_2$ muscarinic agonist pilocarpine. Stimulation of the neuronal $M_2$ receptors with pilocarpine decreases vagally-induced bronchoconstriction by as much as 70–80% (A. D. Fryer, et al., British Journal of Pharmacology (1984) 83:973–978). Loss of function of these $M_2$ receptors is characterized by airway hyperresponsiveness to electrical stimulation of the vagus nerve and by failure of pilocarpine to inhibit vagally-induced bronchoconstriction. Conversely, restoration of $M_2$ receptor function is associated with loss of airway hyperresponsiveness and restoration of the ability of pilocarpine to inhibit vagally-induced bronchoconstriction. This can be demonstrated in a guinea-pig model of allergen-induced asthma, in which loss of $M_2$ receptor function can be restored by administration of heparin (A. D. Fryer, et al., *Journal of Clinical Investigation* (1992) 90:2290–2298).

Specific pathogen free guinea-pigs (Dunkin Hartley; 200–250 g) were injected intraperitoneally (ip) with either saline (control) or 10 mg/kg ovalbumin every other day for three injections. Three weeks after the first injection, the ovalbumin sensitized guinea-pigs (but not the saline injected) were exposed to an aerosol of 5% ovalbumin for 5 min on each of four consecutive days. On day one only (when acute responses to ovalbumin challenge are greatest) pyrilamine (1 mg/kg iv) was administered 60 minutes before challenge. Animals were housed in cages kept within laminar flow hoods throughout this time period.

Twenty-four hours after the last aerosol challenge, the animals were anesthetized with urethane (1.5 g/kg ip). Both external jugular veins were then cannulated for the administration of drugs. Guanethidine (10 mg/kg iv) was given at the start of each experiment to prevent release of norepinephrine from sympathetic nerves. Both vagus nerves were cut in the neck and placed on shielded electrodes immersed in a pool of liquid paraffin. The electrodes were connected to a Grass SD9 stimulator. A heating blanket was used to maintain body temperature at 37 degrees C. The trachea was cannulated and the animals were paralyzed with suxamethonium (infused at 10 ug/kg/min) and ventilated with a positive pressure, constant volume Harvard animal ventilator. Pulmonary inflation pressure (Ppi) was measured at the trachea using a Spectramed pressure transducer. Flow was measured using a Fleish pneumotach with a Grass differential pressure transducer, and this signal was integrated to measure tidal volume. A carotid artery was cannulated for measurement of blood pressure with a Spectramed transducer, and heart rate was derived from the blood pressure using a tachograph. All signals were recorded on a Grass polygraph. $pO_2$ and $pCO_2$ were measured using arterial blood samples taken at the beginning and end of each experiment.

A positive pressure of 100–120 mm $H_2O$ was needed for adequate ventilation of the animals. Given constant flow and volume, bronchoconstriction was measured as the increase in Ppi over the baseline inflation pressure. The Ppi signal was fed into the input of the preamplifier of a second channel on the polygraph, and the baseline Ppi was subtracted electrically. Thus, Ppi was recorded on one channel and increases in Ppi were recorded on a separate channel at a higher sensitivity, so that it was possible to accurately measure increases in Ppi as small as 2 mm $H_2O$ above baseline.

To produce bronchoconstriction, both vagus nerves were stimulated simultaneously at 1 minute intervals (2 or 15 Hz, 0.2 msec pulse duration, 5–30 Volts, 45 pulses per train). This also caused bradycardia. After establishing a stable baseline response to vagal stimulation at 15 Hz, either saline, heparin or O-desulfated heparin was injected intravenously and electrical stimulation of the vagi was continued every minute for the next half-hour. Thirty minutes after either saline, heparin or O-desulfated heparin was injected, and before administration of pilocarpine, control responses to electrical stimulation of the vagus nerves at 2 Hz were obtained. Bronchoconstriction in response to stimulation of the vagus nerves (2 Hz, 0.2 ms, 45 pulses per train) was matched in control and sensitized guinea-pigs by adjusting the voltage (within a range of 5–20 Volts). Thus, the effect of pilocarpine on vagally-induced bronchoconstriction could be compared between groups without concern about different initial bronchoconstrictor responses. Once the parameters for vagally-induced bronchoconstriction at 2 Hz were set and several consistent responses were obtained, pilocarpine (1-100 ug/kg iv) was given in cumulative doses, and the effects on vagally-induced bronchoconstriction measured. Thirty-100 ug/kg iv of pilocarpine produced a transient bronchoconstriction. Therefore, the effect of these doses of pilocarpine on vagally-induced bronchoconstriction was measured after the Ppi had returned to baseline. In previous studies, 2,000 U/kg iv heparin has been shown to be effective at restoring neuronal $M_2$ receptor function (A. D. Fryer, el al., Journal of Clinical Investigation (1992) 90:2290–2298). At the very end of each experiment, atropine (1 mg/kg iv) blocked all responses to vagal nerve stimulation, demonstrating that vagally-induced bronchoconstriction and bradycardia were mediated via muscarinic receptors.

The baseline bronchoconstriction and bradycardia responses to stimulation of the vagus nerves were compared between control and challenged guinea-pigs and treated guinea-pigs using a one-factor analysis of variance. The initial effect of saline, heparin or O-desulfated heparin on vagally-induced bronchoconstriction and bradycardia was analyzed using a one-factor analysis of variance. The effects of saline, heparin and O-desulfated heparin on dose response curves to pilocarpine in antigen challenged and control guinea-pigs were compared using a two-way analysis of variance for repeated measures. The effect of an additional bolus of heparin on the response to 100 ug/kg pilocarpine was tested using a paired t-tests. P values equal to or less than 0.05 were considered significant.

Baseline Ppi, heart rate, and blood pressure were the same in control animals and in animals that were sensitized and challenged with ovalbumin. Treatment with saline, heparin or O-desulfated heparin did not alter either baseline heart rate, pulmonary inflation pressure or blood pressure. Electrical stimulation of both vagus nerves (2 or 15 Hz, 0.2 msec pulse duration, 5–20 Volts, 45 pulses per train) produced bronchoconstriction (measured by the increase in Ppi) and bradycardia. Both of these responses to vagal nerve stimulation were transient and were rapidly reversed after electrical stimulation was stopped. At the end of each experiment, vagally-induced bronchoconstriction and bradycardia were completely blocked by atropine (1 mg/kg), indicating that they were mediated via the release of acetylcholine onto muscarinic receptors.

In guinea-pigs that were not sensitized or challenged with ovalbumin, administration of heparin had no effect on either vagally-induced bronchoconstriction (increase of 27.6±5.4 mm $H_2O$ before heparin vs. 25.2±7.3 mm $H_2O$ 20 minutes post heparin) or bradycardia (fall of 74.3±15 beats/min before heparin vs. 63.4±24 beats/min after heparin). In animals that were antigen challenged, saline had no effect on either vagally-induced bronchoconstriction (see columns 1–2, FIG. 3) or bradycardia (fall of 62.0±26 beats/min before saline vs. 50.0±27 beats/min 20 minutes post saline). In contrast, heparin (2,000 U/kg) reduced vagally-induced bronchoconstriction in sensitized, challenged animals, plateauing at 50% inhibition twenty minutes after administration of heparin (see columns 3–4, FIG. 3). Heparin had no effect on vagally-induced bradycardia (fall of 82.5±6.3 beats/min before heparin vs. 70.0±9.1 beats/min 20 minutes after heparin). The administration of O-desulfated heparin (91.2 mg/kg) also decreased vagally-induced bronchoconstriction, reaching a plateau 20 minutes after administration (see columns 5–6, FIG. 3 and FIG. 4). Like heparin, O-desulfated heparin did not alter vagally-induced bradycardia.

In nonsensitized control animals, pilocarpine (1–100 ug/kg iv) inhibited vagally-induced bronchoconstriction by stimulating $M_2$ muscarinic receptors on the pulmonary parasympathetic nerves (open squares, FIG. 5). This is shown by a progressive reduction in the ratio of bronchoconstriction after pilocarpine compared to bronchoconstriction before pilocarpine. In contrast, pilocarpine had no significant effect on the response to vagal stimulation in sensitized, challenged guinea-pigs (open triangles, FIG. 5), demonstrating that $M_2$ muscarinic receptor activity was impaired in these animals. The response to pilocarpine was restored in a dose dependent fashion by treatment with O-desulfated heparin (FIG. 5), indicating that O-desulfated heparin was active in reversing $M_2$ receptor desensitization, a cause of airways hyperreactivity in these animals. Following the highest dose used, the ability of pilocarpine to inhibit vagally-induced bronchoconstriction in challenged guinea-pigs was completely restored. There was no significant difference between the effect of pilocarpine on vagally-induced bronchoconstriction in control animals (open squares, FIG. 5) and in challenged animals who had received this dose of O-desulfated heparin (closed squares, FIG. 5).

These experiments definitively show that O-desulfated heparin restores the $M_2$ muscarinic receptor desensitization responsible for airways hyperreactivity in asthma. In control animals pilocarpine inhibited vagally-induced bronchoconstriction due to stimulation of inhibitory $M_2$ muscarinic receptors on the parasympathetic nerves of the lung. Pilocarpine-induced inhibition of vagally-induced bronchoconstriction was markedly attenuated following antigen challenge. Thus, in antigen challenged guinea-pigs the neuronal $M_2$ receptors are no longer functioning to inhibit acetylcholine release. This loss of neuronal $M_2$ receptor mediated control of acetylcholine release causes hyperresponsiveness to electrical stimulation of the vagus nerves.

$M_2$ receptor function is restored by O-desulfated heparin. Twenty minutes after O-desulfated heparin was administered, the neuronal receptor in antigen challenged guinea-pigs could once more be stimulated by exogenous agonists, since pilocarpine inhibited vagally-induced bronchoconstriction (FIG. 5). The ability of endogenous acetylcholine to stimulate the neuronal $M_2$ receptors was also restored by O-desulfated heparin, as reflected by the decrease in the bronchoconstrictor response to vagal stimulation in the presence of this non-anticoagulant heparin analog.

Example IV
Treatment of Airways Hyperreactivity in Humans

O-desulfated heparin can be delivered to the lungs by inhalation of an aerosol from an ultrasonic or jet nebulizer generating respirable particles less than 5 microns in mass median aerodynamic diameter (MMAD). While the exact percentage of aerosol actually reaching the lungs varies according to the type of jet or ultrasonic nebulizer used, about 10 percent of the dose in the nebulizer actually reaches the lungs. Newman, S. P., "Therapeutic Aerosols, in Aerosols in the Lung," *Clinical and Experimental Aspects,* S. W. Clarke and D. Pavia, eds., Butterworths: London (1984) pp. 197–224. Therefore, a patient will need to be treated with a nebulizer dose that is ten times the drug actually needed for effective increase in $M_2$ receptor activity.

To calculate the lower end acute dose in a patient
Goal: 0.1–0.2 mg/kg actually reaching the lung
Administer: about 1.0–2.0 mg/kg inhaled by nebulizer
To calculate the average dose for a patient
Goal: 0.5 mg/kg actually reaching the lung
Administer: about 5.0 mg/kg inhaled by nebulizer
To calculate the high end dose for a patient
Goal: 0.7 mg/kg actually reaching the lung
Administer: about 7.0 mg/kg inhaled by nebulizer Based upon the above calculations, O-desulfated heparin can be administered at lower or higher ratios by scaling the dosages up or down. Additionally, the dose can be modified for individual subjects, based upon, for example, the individual. Furthermore, as treatment progresses, the dose can be varied according to therapeutic effects observed with a specific dose. Furthermore, heparin can build up in the lungs to a plateau. Approximately 10% of administered heparin stays bound to the matrix of the lung, bound by heparin-binding proteins (e.g., collagen and fibronectin). Thus a dose strategy can start with a lower end dose and plan for the accumulation of heparin in the lungs over time, particularly for long-term prevention.

The exact amount of such compounds required will vary from subject to subject, depending on the species, age, and general condition of the subject, the severity of the disease that is being treated, the particular compound used, its mode of administration, and the like. Thus, it is not possible to specify an exact activity promoting amount. However, an appropriate amount may be determined by one of ordinary skill in the art using only routine experimentation given the teachings herein.

Example V

Effect of O-Desulfated Heparin on Blood Coagulation

The anti-coagulant potential of the O-desulfated heparin from Example I was studied by determining its effect on the activated partial thromboplastin time (APPT) in vitro. The test was performed in the usual fashion used to monitor the anti-coagulant effect of heparin clinically in patients. The test used 0.1 and 1.0 mg/ml heparin or heparin, O-desulfated according to Example I, added to human test serum in vitro.

TABLE I

| | Control | Heparin | | O-Desulfated Heparin | |
|---|---|---|---|---|---|
| Conc. (mg/ml) | 0 | 1.0 | 0.1 | 1.0 | 0.1 |
| Time to Clot Formation (sec) | 35–45 | >150 | 80 | 42 | 38 |

The O-desulfated heparin from Example I was also studied to determine whether plasma dilutions of 0.1 mg/ml heparin or heparin, desulfated according to Example I, inhibited factor Xa, prolonging test time in an assay for Xa activity utilizing plasma treated with Russell viper venom.

TABLE II

| | Anti-factor Xa Activity | | |
|---|---|---|---|
| Dilution | Control Plasma | Heparin | O-Desulfated Heparin |
| 1:2 | | >8 min. | 42 sec. |
| 1:10 | | >7 min. | 33 sec. |
| 1:100 | | 42 sec. | 32 sec. |
| 1:1000 | | 32 sec. | 32 sec. |
| 0 | 35 sec. | | |

In contrast to heparin, the heparin desulfated according to Example I showed little ability to prolong the APTT and little antifactor Xa activity. Thus, the O-desulfated heparin showed a much reduced anti-coagulant activity when compared to non-desulfated heparin.

Example VI

Culture of Airway Smooth Muscle

Normal adult male Sprague-Dawley rats were sacrificed with pentobartibal overdose. Their tracheas were removed, and the posterior membrane was isolated. The posterior membrane, which contains tracheal smooth muscle, was minced, then digested twice for 30 min at 37° C. in Hanks' balanced salt solution containing 0.2% Type IV collagenase and 0.05% type IV elastase (Sigma Chemical Co., St. Louis, Mo.). Cells were then washed in Dulbecco's modified Eagle's medium (DMEM) with 10% fetal bovine serum (FBS) and seeded in this medium into 25-$cm^2$ plastic flasks at $2\times10^5$ cells/flask. Smooth muscle cell cultures shows the typical "hill and valley" morphologic appearance on phase-contrasts microscopy and stained specifically for α-smooth muscle action. For immunostaining cells were plated overnight on glass slides ($3\times10^4$ cells/slide), washed with phosphate buffered saline (PBS, without calcium and magnesium), and fixed twice for 10 min each with ice cold acetone. Immunostaining was performed using a polyclonal antibody against human α-smooth muscle action and visualized using an avidin-biotin-immunoperoxidase staining kit (Sigma, Product No. IMMH-2).

Example VII

Effect of Serum on Airway Smooth Muscle Proliferation

Cells were plated in 24 well plates at a density of $1.5\times10^4$ cells per well with DMEM containing varying concentrations of FBS (0.25%, 2.5%, 5.0% and 10%). Beginning 24 hours later, cell counts were performed at 24 hour intervals. Wells were washed twice with PBS, then cells were permeabilized by exposure for 10 min to saponin (0.5 mg/ml in PBS). After washing with PBS, cells were then fixed with methanol for 5 min, then stained for 5 min with Geimsa-modified Wright's stain (Sigma) and washed again with PBS. Cell counts of each well were obtained from an average of counts of 10 random fields performed at 40× with a 1 mm³ ocular grid. Table III provides the data obtained.

TABLE III

Cell Numbers - Growth Curve

| Time, Hrs. | FBS Concentration ± SE | | | |
|---|---|---|---|---|
| | 0.25% | 2.5% | 5% | 10% |
| 26 | 1,682 ± 418 | 1,770 ± 434 | 2,390 ± 585 | 2,567 ± 302 |
| 52 | 3,947 ± 321 | 4,323 ± 209 | 8,846 ± 229 | 10,465 ± 514 |
| 74 | 2,955 ± 276 | 6,602 ± 336 | 12,833 ± 1,178 | 18,904 ± 1598 |
| 94 | 2,797 ± 280 | 8,921 ± 267 | 16,142 ± 1,621 | 26,161 ± 3245 |
| 117 | 1,522 ± 188 | 9,664 ± 643 | 19,187 ± 767 | 37,683 ± 1145 |
| 142 | 2,159 ± 225 | 9,664 ± 1130 | 21,683 ± 1,145 | 40,568 ± 1804 |

FIG. 6 graphically demonstrates the results in Table III and shows that FBS stimulates airway smooth muscle proliferation in a dose-dependent manner.

Example VIII
Effect of Heparin and O-Desulfated Heparin on Airway Smooth Muscle Proliferation Airway smooth muscle cells were cultured as above with 10% FBS in the presence of varying concentrations of porcine intestinal mucosal heparin or O-desulfated heparin (0, 2, 20 or 200 μg/ml) added to media immediately after cells were plated. Cell counts were performed after 62 hours. Data is provided in the following Table IV.

TABLE IV

Cell Numbers - Heparin Inhibition

| | Concentration of Heparin | | | |
|---|---|---|---|---|
| | 0 | 2 mg/ml | 20 mg/ml | 200 mg/ml |
| Heparin: | 29,448 ± 2,189 | 25,686 ± 1,893 | 17,671 ± 1,087 | 14,556 ± 1315 |
| O-desulfated heparin: | 30,671 ± 2,067 | 25,233 ± 714 | 20,192 ± 1,279 | 16,057 ± 1156 |

FIG. 7 graphically demonstrates the data in Table IV and shows that heparin and O-desulfated heparin equally inhibited proliferation of airway smooth muscle in a dose dependent manner. The highest dose of either heparin (200 μg/ml) inhibited cell growth by approximately 50%.

Example IX
Effect of Heparins and O-Desulfated Heparins on Complement-Mediated Red Cell Lysis Complement-mediated red blood cell hemolysis was assessed by modification of a technique described previously (Friedrichs el al. (1994) Circ. Res. 75:701–710). Human blood was collected and centrifuged at 2000× g for 10 min at room temperature. The plasma layer was discarded, and the red blood cells were washed three times with PBS. A solution of 10% erythrocytes was prepared in assay buffer (PBS containing 0.25% bovine serum albumin, pH 7.4). The assay for detection of hemolysis was performed by measuring the absorbance of the assay solution at 540 nm, the major peak for hemoglobin. Whole rabbit plasma (500 μl) and PBS (500 μl) or the heparins tested (500 μl in PBS, 1 mg/ml final concentration) were mixed in siliconized tubes. Human red cells (0.5% final concentration) were added and the tubes were incubated in a shaker water bath at 37° C. for 30 min. Tubes were centrifuged at 1000× g for 10 min and absorbance of the supernatant was read immediately at 540 nm and compared to a blank containing plasma and PBS alone. Percent hemolysis was determined by the ratio of $A_{540}$ for heparin-treated and untreated control tubes. Results were expressed as percent inhibition (100-% hemolysis).

Heparin was an effective inhibitor of complement-mediated red cell hemolysis (71±4% inhibition at 1 mg/ml (n=3). ODS heparin was likewise a potent inhibitor of complement-induced lysis of red cells in this system, inhibiting hemolysis by 73±2% (n=3). These results confirm that inhibition of complement by heparin is not dependent on antithrombin III binding or other anticoagulant functions. These results additionally demonstrate that O-desulfated heparin has equivalent effectiveness as heparin in inhibition of complement-mediated red cell hemolysis.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A method of treating a patient suffering from asthma comprising administering to the patient a pharmaceutical composition having an asthmatic response-reducing amount of O-desulfated heparin having O-desulfation at least at the 2-O and 3-O positions.

2. The method of claim 1, wherein said pharmaceutical composition is administered by inhalation.

3. The method of claim 1, wherein said pharmaceutical composition is administered orally.

4. The method of claim 1, wherein said pharmaceutical composition is administered by intravenous injection.

5. The method of claim 1, wherein said pharmaceutical composition further comprising a pharmaceutically acceptable carrier.

6. The method of claim 1, wherein said asthmatic response-reducing amount is from about 1 mg to about 100 mg per kilogram of the body weight of the patient.

7. The method of claim 1, wherein said O-desulfated heparin has an average molecular weight of from about 100 to about 8000.

8. The method of claim 1, wherein said O-desulfated heparin is a modified O-desulfated heparin selected from the group consisting of periodate-oxidized O-desulfated heparin, decarboxylated O-desulfated heparin, acetylated O-desulfated heparin, deacetylated O-desulfated heparin, and deacetylated oxidized O-desulfated heparin.

9. The method of claim 1, wherein said O-desulfated heparin is at least 50% desulfated at the 2-O position and is at least 50% desulfated at the 3-O position.

10. The method of claim 1, wherein said O-desulfated heparin is at least 90% desulfated at the 2-O position and is at least 90% desulfated at the 3-O position.

11. The method of claim 1, wherein said O-desulfated heparin is made by a process comprising alkalinizing a heparin solution to a pH value of at least 13, adjusting the pH to neutral, and lyophilizing the solution.

12. The method of claim 1, wherein said patient is suffering from antigen-induced asthma.

13. The method of claim 1, wherein the method reduces asthmatic response at least by reducing airways hyperactivity in the patient.

14. The method of claim 1, wherein the method reduces asthmatic response at least by increasing the activity of desensitized $M_2$ muscarinic receptors in the patient.

15. The method of claim 1, wherein the method reduces asthmatic response at least by reducing bronchoconstriction in the patient.

16. The method of claim 1, wherein the method reduces asthmatic response at least by reducing airway smooth muscle cell proliferation in the patient.

17. The method of claim 1, wherein the method reduces asthmatic response at least by inhibiting complement-mediated hemolysis in the patient.

18. A method of preventing asthmatic response in a patient comprising administering to the patient, prior to any asthmatic response in the patient, a pharmaceutical composition having a pharmaceutically effective amount of O-desulfated heparin having O-desulfation at least at the 2-O and 3-O positions.

19. The method of claim 18, wherein said pharmaceutical composition is administered by inhalation.

20. The method of claim 18, wherein said pharmaceutical composition is administered orally.

21. The method of claim 18, wherein said pharmaceutical composition is administered by intravenous injection.

22. The method of claim 18, wherein said pharmaceutical composition further comprising a pharmaceutically acceptable carrier.

23. The method of claim 18, wherein said asthmatic response-reducing amount is from about 1 mg/kg to about 100 mg/kg.

24. The method of claim 18, wherein said O-desulfated heparin has an average molecular weight of from about 100 to about 12,000.

25. The method of claim 18, wherein said O-desulfated heparin is a modified O-desulfated heparin selected from the group consisting of periodate-oxidized O-desulfated heparin, decarboxylated O-desulfated heparin, acetylated O-desulfated heparin, deacetylated O-desulfated heparin, and deacetylated oxidized O-desulfated heparin.

26. The method of claim 18, wherein said O-desulfated heparin is at least 50% desulfated at the 2-O position and is at least 50% desulfated at the 3-O position.

27. The method of claim 18, wherein said O-desulfated heparin is at least 90% desulfated at the 2-O position and is at least 90% desulfated at the 3-O position.

28. The method of claim 18, wherein said O-desulfated heparin is made by a process comprising alkalinizing a heparin solution to a pH value of at least 13, lyophilizing the solution, and then adjusting the pH back to neutral.

29. The method of claim 18, wherein said patient has had a history of asthmatic reaction.

30. The method of claim 18, wherein the method prevents asthmatic response at least by reducing airways hyperactivity in the patient.

31. The method of claim 18, wherein the method prevents asthmatic response at least by increasing the activity of desensitized $M_2$ muscarinic receptors in the patient.

32. The method of claim 18, wherein the method prevents asthmatic response at least by reducing bronchoconstriction in the patient.

33. The method of claim 18, wherein the method prevents asthmatic response at least by reducing airway smooth muscle cell proliferation in the patient.

34. The method of claim 18, wherein the method prevents asthmatic response at least by inhibiting complement-mediated hemolysis in the patient.

* * * * *